United States Patent
Seo et al.

(10) Patent No.: US 7,311,901 B2
(45) Date of Patent: Dec. 25, 2007

(54) AMPHIPHILIC BLOCK COPOLYMER AND POLYMERIC COMPOSITION COMPRISING THE SAME FOR DRUG DELIVERY

(75) Inventors: Min Hyo Seo, Daejeon (KR); Bong Oh Kim, Daejeon (KR); In Ja Choi, Daejeon (KR); Myung Seob Shim, Seoul (KR)

(73) Assignee: Samyang Corporation, Seoul (KR)

( * ) Notice: Subject to any disclaimer, the term of this patent is extended or adjusted under 35 U.S.C. 154(b) by 0 days.

(21) Appl. No.: 10/962,204

(22) Filed: Oct. 7, 2004

(65) Prior Publication Data

US 2005/0201972 A1    Sep. 15, 2005

Related U.S. Application Data

(60) Provisional application No. 60/514,367, filed on Oct. 24, 2003.

(30) Foreign Application Priority Data

Oct. 10, 2003    (KR) ............... 10-2003-0070667

(51) Int. Cl.
*A61K 31/74* (2006.01)
*A61K 47/48* (2006.01)
*C08L 39/04* (2006.01)

(52) U.S. Cl. .............. 424/78.27; 424/78.08; 424/78.17; 525/205

(58) Field of Classification Search .............. None
See application file for complete search history.

(56) References Cited

U.S. PATENT DOCUMENTS

| | | |
|---|---|---|
| 4,451,618 A | 5/1984 | Okamoto |
| 4,479,911 A | 10/1984 | Fong |
| 5,429,826 A | 7/1995 | Nair et al. |
| 5,449,513 A | 9/1995 | Yokoyama et al. |
| 6,080,396 A | 6/2000 | Yokoyama et al. |
| 6,267,987 B1 | 7/2001 | Park et al. |
| 6,322,805 B1 | 11/2001 | Kim et al. |
| 6,383,500 B1 | 5/2002 | Wooley et al. |
| 6,410,057 B1 | 6/2002 | Kweon-Choi et al. |
| 6,458,373 B1 | 10/2002 | Lambert et al. |
| 6,569,528 B2 | 5/2003 | Nam et al. |
| 6,589,548 B1 | 7/2003 | Oh et al. |
| 6,616,941 B1 | 9/2003 | Seo et al. |
| 2003/0022991 A1 | 1/2003 | Kennedy et al. |
| 2003/0166779 A1 | 9/2003 | Khemani et al. |

FOREIGN PATENT DOCUMENTS

| | | |
|---|---|---|
| EP | 0 330180 A1 | 2/1989 |
| EP | 0 552 802 A2 | 1/1993 |
| EP | 0 583 955 A2 | 8/1993 |
| EP | 0 645145 | 9/1994 |
| JP | 206815 | 7/1994 |
| WO | WO 99/29758 | 6/1999 |
| WO | WO 01/12718 | 2/2001 |
| WO | WO 03/033592 A1 | 4/2003 |

*Primary Examiner*—Michael G. Hartley
*Assistant Examiner*—Jake M. Vu
(74) *Attorney, Agent, or Firm*—Thorpe North & Western LLP

(57) ABSTRACT

The present invention relates to an amphiphilic block copolymer of a hydrophilic block and a hydrophobic block with a terminal hydroxyl group wherein the terminal hydroxyl group of the hydrophobic bock is substituted with a tocopherol or cholesterol group. It also relates to polymeric compositions capable of forming stable micelles in an aqueous solution, comprising the amphiphilic block copolymer and a polylactic acid derivative wherein one or more ends of the polylactic acid are covalently bound to at least one carboxyl group.

7 Claims, 13 Drawing Sheets

AMPHIPHILIC BLOCK COPOLYMER AND POLYMERIC COMPOSITION COMPRISING THE SAME FOR DRUG DELIVERY

CROSS-REFERENCE TO RELATED APPLICATIONS AND CLAIMS OF PRIORITY

Priority to U.S. Provisional Patent Application Ser. No. 60/514,367 filed on Oct. 24, 2003 and Korean Patent Application No. 2003-0070667 filed on Oct. 10, 2003 is claimed.

TECHNICAL FIELD

This invention relates to an amphiphilic block copolymer comprising a hydrophilic A block and a hydrophobic B block with a terminal hydroxyl group, wherein said terminal hydroxyl group of the hydrophobic block is substituted with a tocopherol or cholesterol group. The invention further relates to a polymeric composition comprising said amphiphilic block copolymer and a polylactic acid derivative wherein one or more ends of the polylactic acid are covalently bound to at least one carboxyl group. It still further relates to a metal ion-fixed polymeric composition, wherein the carboxyl terminal group of the polylactic acid derivative is fixed with a di- or tri-valent metal ion.

BACKGROUND ART

When a drug is administered into the body, only a small amount of the drug may reach its target site and most of the administered dose is distributed to non-targeted sites and may cause undesirable side effects. Therefore, in the last two decades, research has focused on the development of systems efficient for site specific delivery of drugs by the use of appropriate carriers, which include liposomes, small molecular surfactant micelles, polymeric nanoparticles, and polymeric micelles (polymeric nanoparticles made of hardened micelles). The use of liposomes as drug carriers has been found to be limited mainly due to such problems as low entrapment efficiency, drug instability, rapid drug leakage, and poor storage stability. Small molecular surfactant micelles are easily dissociated when they are diluted in body fluids after been administered into the body, and therefore it is difficult for them to perform sufficiently as drug carriers.

Recently, polymeric nanoparticles and polymeric micelles using biodegradable polymers have been reported to be extremely useful technologies for overcoming these problems. They change the in vivo distribution of an intravenously administered drug thereby reducing its side effects and improving its efficacy thereby offering such advantages as cell specific targeting and control of the release of the drug. They also have good compatibility with body fluids and improve the solubility and bioavailability of poorly water-soluble drugs.

Nanometer size drug carriers with hydrophilic surfaces have been found to evade recognition and uptake by the reticulo-endothelial systems(RES), and thus to circulate in the blood for a long period of time. Another advantage of these hydrophilic nanoparticles is that, due to their extremely small size, the particles extravagate at the pathological sites, such as solid tumors, through a passive targeting mechanism. However, successful drug delivery to the specific target site requires stable retention of the drug by a carrier while in the circulation. Since drug targeting appears to require a long circulation time and the carrier is exposed to blood components for a long period of time, the stability of a drug-carrier association needs to be improved over that of carriers that are rapidly cleared.

Among the nanometer size drug carriers with hydrophilic surfaces, polymeric micelles usually consist of several hundreds of block copolymers and have a diameter of about 20 nm to 50 nm. The polymeric micelles have two spherical co-centric regions, a densely packed core of hydrophobic material which is responsible for entrapping the hydrophobic drug, and an outer shell made of hydrophilic material for evasion of the body's RES which permits circulation in the blood for a longer period of time. In spite of their distinct advantages such as small size, high solubility, simple sterilization, and controlled drug release, the physical stability of these carriers is a critical issue since the rapid release of the incorporated drug may occur in vivo.

Micelles are thermodynamically stable if the total copolymer concentration is above the critical micelle concentration (CMC). Thus, the use of a copolymer system with a low CMC value may increase the in vivo stability of the micelles. The kinetic stability means the rate of disassembly of a micelle. The rate of disassembly depends upon the physical state of the micelle core. Micelles formed from copolymers containing a hydrophobic block which has a high glass transition temperature will tend to disassemble more slowly than those with a low glass transition temperature. They are also likely to be affected by many of the same factors that affect the rate of unimer exchange between micelles. The unimer exchange rate has been found to be dependent on many factors such as the content of solvent within the core, the hydrophobic content of the copolymer, and the lengths of both the hydrophilic and hydrophobic blocks.

Great efforts have been devoted to the development of a biodegradable and biocompatible core-shell type drug carrier with improved stability and efficacy, which will entrap a poorly water-soluble drug. A preparation method of chemically fixing polymeric micelles, wherein the polymer is a core-shell type polymer comprising a hydrophilic polyethylene oxide as the shell and a hydrophobic biodegradable polymer that is cross-linked in an aqueous solution as the core, was disclosed in EP 0,552,802A2. However, these polymeric micelles are difficult to prepare because a cross linker must be introduced into the hydrophobic component of the A-B type di-block or A-B-A type tri-block copolymer so that the core-forming polymer has a stable structure. Also, using a cross linker that has never been used before in a human body raises safety concerns.

A micelle forming block copolymer-drug complex was disclosed in U.S. Pat. No. 6,080,396. The high molecular block copolymer-drug complex in which the high molecular weight block copolymer, having a hydrophilic polymer segment and a hydrophobic polymer segment, forms a micelle having the hydrophilic segment as its outer shell and contains an anthracycline anticancer agent in its hydrophobic inner core. The molecules of the anticancer agent are covalently linked within the micellar core. However, when the drug is covalently linked within the polymeric micelles, it is difficult to control the cleavage rate of the drug-copolymer linkage.

On the other hand, a report shows that the solubilization of a hydrophobic drug can be achieved by a polymeric micelle composed of a di- or tri-block copolymers comprising a hydrophilic polymer of polyalkylene glycol derivatives and a hydrophobic biodegradable polymer such as fatty acid polyesters or polyamino acids. U.S. Pat. No. 5,449,513 discloses a di-block copolymer comprising polyethylene glycol as the hydrophilic polymer, and a polyamino acid derivative, e.g. polybenzyl aspartic acid, etc., as the hydrophobic polymer. This di-block copolymer can solubilize hydrophobic anticancer agents, e.g. doxorubicin, or anti-inflammatory agents, e.g. indomethacin. However, the polyamino acid derivative cannot be hydrolyzed in vivo, and thus causes side effects due to immune responses that are excited One approach to improve the stability of polymeric micelles is to increase the hydrophobicity of the polymer. To do so, the molecular weight or the concentration of the polymer should be adjusted. However, as the molecular weight is increased, its biodegradability is decreased, and so the polymer is poorly excreted from the body and accumulates in organs causing toxic effects therein. U.S. Pat. No. 5,429,826 discloses a di- or multi-block copolymer comprising a hydrophilic polyalkylene glycol and a hydrophobic polylactic acid. Specifically, this patent describes a method of stabilizing polymeric micelles by micellizing a di- or multi-block copolymer wherein an acrylic acid derivative is bonded to a terminal group of the di- or multi-block copolymer, and then, in an aqueous solution, the polymer is crosslinked in order to form the micelles. The above method could accomplish stabilization of the polymeric micelle, but the crosslinked polymer is not degraded, and thus, cannot be applied for in vivo use. The above polymeric micelles can solubilize a large amount of poorly water-soluble drug in an aqueous solution with a neutral pH, but the drawback a that the drug is released within a short period of time. Also, in U.S. Pat. No. 6,458,373, a poorly water-soluble drug is solubilized into the form of an emulsion with α-tocopherol. According to this patent, to stabilize the emulsion, PEGylated vitamin E is used as a surfactant. PEGylated vitamin E has a similar structure to the amphiphilic block copolymer comprised of a hydrophilic block and a hydrophobic block, and the highly hydrophobic tocopherol increases the copolymer's affinity with a poorly water-soluble drug, and thus, it can solubilize the poorly water-soluble drug. However, polyethylene glycol used as the hydrophilic polymer has a limited molecular weight, and so PEGylated vitamin E alone can solubilize a hydrophobic drug such as paclitaxel only up to 2.5 mg/ml. At 2.5 mg/ml or more, unstable micelles are formed, and the drug crystals are likely to form precipitates.

Clinical tumor resistance to chemotherapy can be inherent or acquired. Inherent resistance is present in the tumors that fail to respond to the first-line chemotherapy at the time of diagnosis. Acquired resistance occurs in the tumors that are often highly responsive to the initial treatment, but on recurrence, exhibit an entirely different phenotype. The resistance can be formed to both previously used drugs and new drugs with different structures and mechanisms of action. For example, cancer chemotherapy with Taxol® often fails due to the acquired resistance of cancer cells, which is frequently associated with the overexpression of P-gp and alteration of β-tubulin. Taxol® resistant cells exhibit cross-resistance to other drugs including actinomycin D, doxorubicin, vinblastine, and vincristine. Therefore, clinical drug resistance is a major barrier to be overcome before chemotherapy can be curative for patients with metastatic cancer.

Drug-resistant cancer cells show a higher a $IC_{50}$ (50% cell inhibition concentration of drug), and so for chemotherapy to be effective a higher concentration of drugs is needed for the tumor cells while reduced drug concentration is desired for the normal cells. Therefore, longer systemic circulation and specific localization of drugs in the tumor tissues are required for improving the effectiveness against drug-resistant cancers.

In view of the foregoing, the development of an improved polymeric micelle composition for hydrophobic drug delivery that is biocompatible and biodegradable has been appreciated and desired. The present invention provides such an improved polymeric micelle composition which is biocompatible and biodegradable, and can effectively deliver a hydrophobic drug without a decrease in its stability.

SUMMARY OF THE INVENTION

One aspect of the present invention relates to an amphiphilic block copolymer comprising a hydrophilic A block and a hydrophobic B block with a terminal hydroxyl group, wherein said terminal hydroxyl group of the hydrophobic block is substituted with a tocopherol or cholesterol group, and to a preparation process thereof. The amphiphilic block copolymer of the present invention has remarkably increased hydrophobicity of the hydrophobic block while maintaining almost the same molecular weight as the native polymer. Also, the hydrophobic functional group remarkably improves affinity with a poorly water-soluble drug, and thus polymeric micelles formed from the polymer are more stable in aqueous solutions, and can maintain the poorly water-soluble drug solubilized therein at an increased plasma concentration for an extended period of time. Furthermore, the amphiphilic block copolymer may be mixed with other polymers, and be prepared into a polymeric composition for drug delivery.

Another aspect of the present invention relates to a polymeric composition comprising an amphiphilic block copolymer of a hydrophilic A block and a hydrophobic B block with a terminal hydroxyl group, and a polylactic acid derivative, wherein said terminal hydroxyl terminal group of the hydrophobic B block is substituted with a tocopherol or cholesterol group, and at least one end of the polylactic acid derivative is covalently bound to at least one carboxyl group.

The third aspect of the present invention relates to a polymeric composition comprising an amphiphilic block copolymer of a hydrophilic A block and a hydrophobic B block with a terminal hydroxyl group, and a polylactic acid derivative, wherein said terminal hydroxyl terminal group of the hydrophobic B block is substituted with a tocopherol or cholesterol group, and at least one end of the polylactic acid derivative is covalently bound to at least one carboxyl group, wherein the carboxyl terminal group of the polylactic acid derivative is fixed with a di- or tri-valent metal ion.

The polymeric compositions of the present invention can form stable polymeric micelles or nanoparticles in body fluids or aqueous solutions. The micelles or nanoparticles formed from the compositions of the present invention have a hydrophilic outer shell and a hydrophobic inner core wherein a large amount of hydrophobic drug can be physically trapped. The drug-containing micelles and nanoparticles of the present invention have a prolonged retention time in the bloodstream after administration, and can be utilized to make various pharmaceutical formulations. The anticancer drug-containing polymeric micelles prepared from the composition of the present invention can be efficiently transferred to, and effectively act on, anticancer drug-resistant cancer cells. Additional features and advantages of the invention will be apparent from the detailed description that follows, taken in conjunction with the accompanying drawings, which together illustrate, by way of example, the features of the present invention.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1:
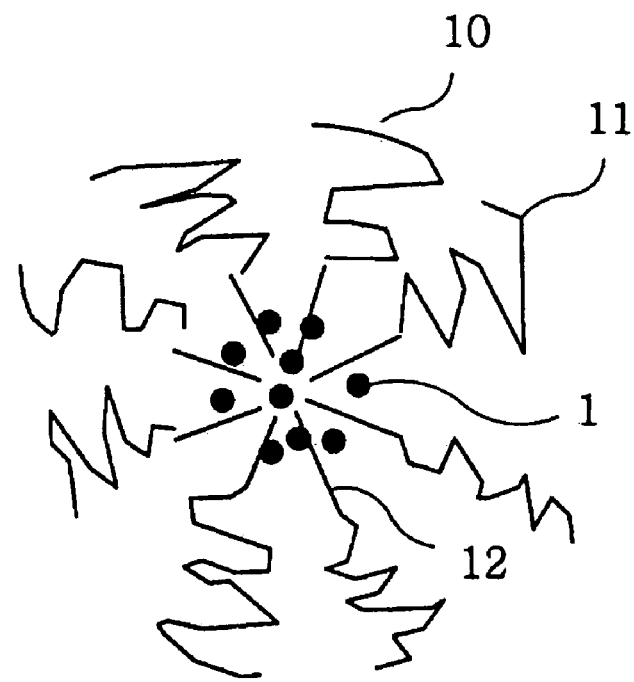
FIG. 1 is a schematic diagram of a polymeric micelle formed by monomethoxypolyethylene glycol-polylactide-hydrophobic moiety (mPEG-PLA-hydrophobic moiety) in an aqueous environment.

Reference will now be made to the exemplary embodiments illustrated, and specific language will be used herein to describe the same. It will nevertheless be understood that no limitation of the scope of the invention is thereby intended.

DETAILED DESCRIPTION OF THE INVENTION

Before the present polymeric compositions and methods of using and making thereof are disclosed and described, it should be understood that this invention is not limited to the particular configurations, process steps, and materials disclosed herein, and such configurations, process steps, and materials may be varied. It should be also understood that the terminology employed herein is used for the purpose of describing particular embodiments only and is not intended to limit the scope of the present invention which will be limited only by the appended claims and equivalents thereof.

It should be noted that, in this specification and the appended claims, the singular form, "a," "an," or "the", includes plural referents unless the context clearly dictates otherwise. Thus, for example, the reference to a polymer containing "a terminal group" includes reference to two or more such groups, and reference to "a hydrophobic drug" includes reference to two or more such drugs. Further, reference to an amphiphilic block copolymer includes mixtures of block copolymers provided that the compositions of each A and B block, the respective ratios of each block, and weight or number average molecular weight of each block and/or the overall block polymeric composition fall within the limitations defined herein.

In describing and claiming the present invention, the following terminology will be used in accordance with the definitions set out below.

As used herein, the term "bioactive agent" or "drug" or any other similar term means any chemical or biological material or compound that is suitable for administration in view of the methods previously known in the art and/or the methods taught in the present invention and that induces a desired biological or pharmacological effect. Such effects may include but are not limited to (1) having a prophylactic effect on the organism and preventing an undesired biological effect such as preventing an infection, (2) alleviating conditions caused by diseases, for example, alleviating pain or inflammation caused as a result of diseases, and/or (3) either alleviating, reducing, or completely eliminating a disease from the organism. The effect may be local, such as providing a local anesthetic effect, or may be systemic.

As used herein, the term "biodegradable" or "biodegradation" is defined as the conversion of materials into less complex intermediates or end products by solubilization hydrolysis, or by the action of biologically formed entities which can be enzymes or other products of the organism.

As used herein, the term "biocompatible" means materials or the intermediates or end products of materials formed by solubilization hydrolysis, or by the action of biologically formed entities which can be enzymes or other products of the organism and which cause no adverse effect on the body.

As used herein, an "effective amount" means the amount of bioactive agent that is sufficient to provide the desired local or systemic effect at a reasonable risk/benefit ratio as would attend any medical treatment.

As used herein, "administering" and similar terms mean delivering the composition to an individual being treated such that the composition is capable of being circulated systemically. Preferably, the compositions of the present invention are administered by the subcutaneous, intramuscular, transdermal, oral, transmucosal, intravenous, or intraperitoneal routes. Injectables for such use can be prepared in conventional forms, either as a liquid solution or suspension, or in a solid form that is suitable for preparation as a solution or suspension in liquid prior to injection, or as an emulsion. Suitable excipients that can be used for administration include, for example, water, saline, dextrose, glycerol, ethanol, and the like; and if desired, minor amounts of auxiliary substances such as wetting or emulsifying agents, buffers, and the like. For oral administration, they can be formulated into various forms such as solutions, tablets, capsules, etc.

Below, the exemplary embodiments are shown and specific language will be used herein to describe the same. It should nevertheless be understood that no limitation of the scope of the invention is thereby intended. Alterations and further modifications of the inventive features illustrated herein, and additional applications of the principles of the present invention as illustrated herein, for one skilled in the relevant art, in connection with this disclosure, should be considered within the scope of the present invention.

In one aspect, the present invention provides an amphiphilic block copolymer comprising a hydrophilic A block and a hydrophobic B block with a terminal hydroxyl group, wherein said terminal hydroxyl group of the hydrophobic block is substituted with a tocopherol or cholesterol group.

The present invention also provides a process for preparing the amphiphilic block copolymer, e.g. process variants I to III below:

Process Variant I:
A process comprising the steps of:
1) carboxylating a hydrophobic compound having a tocopherol or cholesterol group; and
2) reacting an amphiphilic block copolymer comprised of a hydrophilic A block and a hydrophobic B block having a terminal hydroxyl group with the carboxylated hydrophobic compound resulted from step 1, in the presence of dicyclohexylcarbodiimide (DCC) as an initiator, to allow the carboxylated hydrophobic compound be chemically bound to the terminal hydroxyl group of the hydrophobic B block.

Process Variant II:
A process comprising the steps of:
1) carboxylating a hydrophobic compound having a tocopherol or cholesterol group and activating the resulting carboxylated hydrophobic compound with oxalyl chloride; and
2) reacting an amphiphilic block copolymer comprised of a hydrophilic A block and a hydrophobic B block having a terminal hydroxyl group with the activated carboxylated hydrophobic compound resulted from step 1, to allow the carboxylated hydrophobic compound be chemically bound to the terminal hydroxyl group of the hydrophobic B block.

Process Variant III:
A process comprising the steps of:
1) mixing a hydrophobic compound having a tocopherol or cholesterol group with a dichloride compound as a linkage agent;
2) adding an amphiphilic block copolymer comprising a hydrophilic A block and a hydrophobic B block having a terminal hydroxyl group to the reaction mixture of step 1, to allow the hydrophobic compound be chemically bound to the terminal hydroxyl group of the hydrophobic B block; and
3) dissolving and precipitating the block copolymer obtained in step 2).

The term "a carboxylated hydrophobic compound" refers to a hydrophobic compound with a hydroxyl group to which a carboxyl group is bound, and the carboxyl group may be derived from succinate, malonate, glutarate, or adipate.

The present invention also provides a drug carrier comprising the amphiphilic block copolymer of the present invention. It also provides a pharmaceutical composition capable of forming polymeric micelles in a body fluid or an aqueous solution, comprising said amphiphilic block copolymer and a poorly water-soluble drug.

The amphiphilic block copolymer of the present invention is preferably an A-B type diblock copolymer or B-A-B type triblock copolymer comprising a hydrophilic A block and a hydrophobic B block, and the terminal group of the hydrophobic block is a hydroxyl group. The amphiphilic block copolymer of the present invention, when placed in an aqueous environment, forms a core-shell type of polymeric micelle wherein the hydrophobic B block forms the core and the hydrophilic A block forms the shell. Preferably, the hydrophilic A block is a member selected from the group consisting of polyalkylene glycol, polyvinyl alcohol, polyvinyl pyrrolidone, polyacryl amide, and derivatives thereof. More preferably, the hydrophilic A block is a member selected from the group consisting of monomethoxypolyethylene glycol, monoacetoxypolyethylene glycol, polyethylene glycol, polyethylene-co-propylene glycol, and polyvinyl pyrrolidone. Preferably, the hydrophilic A block has a number average molecular weight of 200 to 50,000 Daltons. More preferably, the hydrophilic A block has a number average molecular weight of 1,000 to 20,000 Daltons.

The hydrophobic B block of the amphiphilic block copolymer of the present invention is a highly biocompatible and biodegradable polymer selected from the group consisting of polyesters, polyanhydrides, polyamino acids, polyorthoesters and polyphosphazine. More preferably, the hydrophobic B block is one or more selected from the group consisting of polylactides, polyglycolides, polycaprolactone, polydioxan-2-one, polylactic-co-glycolide, polylactic-co-dioxan-2-one, polylactic-co-caprolactone and polyglycolic-co-caprolactone. Preferably, the hydrophobic B block of the amphiphilic block copolymer has a number average molecular weight of 50 to 50,000 Daltons. More preferably, the hydrophobic B block of the amphiphilic block copolymer has a number average molecular weight 200 to 20,000 Daltons.

The hydrophobic B block has a hydroxyl terminal group, and the hydroxyl terminal group is substituted with tocopherol or cholesterol both having excellent hydrophobicity, which increases the hydrophobicity of the hydrophobic B block. When placed in an aqueous solution, the hydrophobic block of the amphiphilic block copolymer of the present invention avoids contact with water, and forms an inner core, to form a spherical polymeric micelle. Thus, when a poorly water-soluble drug is introduced into the amphiphilic block copolymer, the poorly water-soluble drug is surrounded by the hydrophobic polymer, the inner core of the polymeric micelle, and thus, can be entrapped within the micelle. The stability of the formed micelle depends on the hydrophobicity of the hydrophobic block and its affinity with the drug. Therefore, in the present invention, in order to increase the hydrophobicity of the hydrophobic block while maintaining its molecular weight, a functional group with excellent hydrophobicity, e.g. tocopherol, cholesterol, etc. is chemically bound thereto using a linkage agent. Tocopherol and cholesterol are biological compatible and hydrophobic compounds having a ring structure, which can increase the affinity of the block copolymer with a poorly water-soluble drug.

The ratio of the hydrophilic A block to the hydrophobic B block of the amphiphilic block copolymer of the present invention is preferably within the range of 30:70 to 97:3 by weight, and more preferably within the range of 4:6 to 7:3. If the content of the hydrophilic A block is too low, the polymer may not form polymeric micelles in an aqueous solution, and if the content is too high, the polymeric micelles formed therefrom are not stable.

In one embodiment, the amphiphilic block copolymer of the present invention may be represented by the following Formula:

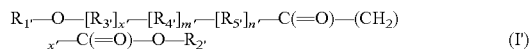
(I')

wherein $R_{1'}$ is $CH_3$—, H—[$R_{5'}$]$_{n'}$—[$R_{4'}$]$_{m'}$—, or $R_{2'}$—O—C(=O)—(CH$_2$)$_{x'}$—C(=O)—[$R_{5'}$]$_{n'}$—[$R_{4'}$]$_{m'}$—;

$R_{2'}$ is tocopherol or cholesterol;

$R_{3'}$ is —CH$_2$CH$_2$—O—, —CH(OH)—CH$_2$—, —CH(C(=O)—NH$_2$)—CH$_2$—, or;

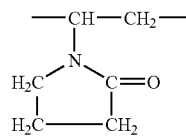

$R_{4'}$ is —C(=O)—CHZ'-O—, wherein Z' is a hydrogen atom or methyl group;

$R_{5'}$ is —C(=O)—CHY"—O—, wherein Y" is a hydrogen atom or methyl group, —C(=O)—CH$_2$CH$_2$CH$_2$CH$_2$CH$_2$—O—, or —C(=O)—CH$_2$OCH$_2$CH$_2$—O—;

l' is an integer from 4-1150;
m' is an integer from 1-300;
n' is an integer from 0-300; and
X' is an integer from 0-4.

As compared with prior amphiphilic block copolymers, the copolymer with the hydrophobic group-substituted hydrophobic block of the present invention has increased hydrophobicity, a decreased critical micelle concentration (CMC), and increased affinity with a poorly water-soluble drug, and thus, contains the drug in a stable environment. Furthermore, the size of the micelles formed in an aqueous solution is increased due to the functional group bound at the end, and thus, a sufficient amount of drug can be contained in the micelle. Therefore, the amphiphilic block copolymer can be efficiently used as a drug carrier. The functional group with strong hydrophobicity introduced in the present invention has a high molecular-weight; thus it can remarkably increase both the hydrophobicity and the affinity of the block copolymer with the drug and thus significantly stabilize the drug containing micelles.

In addition, the polymeric micelle formed from the amphiphilic block copolymer of the present invention has a prolonged in vivo retention time. The blood concentration of the drug in the polymeric micelles depends on hydrophobic moiety substituted on for the hydroxyl terminal group of hydrophobic B block of the amphiphilic diblock copolymers. As shown in Table 6 and FIG. 8, the polymeric micelles (Compositions 1-2) of the amphiphilic block copolymers with a hydrophobic moiety (tocopherol or cholesterol) substituted on the hydroxyl terminal group of hydrophobic B block had a much longer bloodstream retention time than the original mPEG-PLA-OH polymeric micelles (Composition 3). Moreover, mPEG-PLA-tocopherol micelles (Composition 1) circulated the longest in the blood among all the polymeric micelles. This result can be explained by the increased hydrophobicity of tocopherol and cholesterol moiety in the hydrophobic B block.

The block copolymer having the hydrophobic block whose hydroxyl terminal group is substituted with tocopherol or cholesterol can be prepared according to the following methods. In one embodiment, a suitable linker, e.g. a dicarboxylic acid such as succinic acid, malonic acid, glutaric acid or adipic acid, is introduced into the hydroxyl group of tocopherol or cholesterol, and the carboxylated tocopherol or cholesterol is chemically bound to the hydroxyl terminal group of the hydrophobic B block.

In one embodiment, according to the method of U.S. Pat. No. 6,322,805, the amphiphilic block copolymer (mPEG-PLA) comprised of monomethoxypolyethylene glycol (mPEG; Mn=20,000) and polylactide (PLA; Mn=1,750) is weighed, and dehydrated using a vacuum pump at 120° C., and then dissolved in acetonitrile or methylene chloride. Thereto is added tocopherol succinate or cholesterol succinate, and dicyclohexylcarbodiimide (DCC) and 4-dimethylaminopyridine (DMAP) are weighed and added thereto as an initiator and a catalyst, respectively, and the reaction is performed at room temperature. The reactant becomes opaque due to dicyclohexylurea (DCU) formed in the reaction between the terminal —OH of mPEG-PLA and —COOH of the hydrophobic compound. After 24 hours, DCU is removed by using a glass filter, and DMAP is extracted and removed with a hydrochloric acid aqueous solution. To this purified product solution is added MgSO$_4$ to remove any residual moisture, and then, precipitates are formed in a hexane/diethyl ether solvent in order to obtain the amphiphilic block copolymer to which tocopherol succinyl or cholesterol succinyl is bound, mPEG-PLA-tocopherol or mPEG-PLA-cholesterol (in which tocopherol or cholesterol is bound to PLA via succinic acid diester). The precipitated polymeric product is filtered, and then dried under vacuum to obtain the polymer as white particles.

In another embodiment, a carboxylated hydrophobic compound is activated with oxalyl chloride without any catalyst, and bound to the end of mPEG-PLA. That is, tocopherol (or cholesterol) succinate is reacted with oxalyl chloride, and then, excessive oxalyl chloride is removed under vacuum at room temperature. The mPEG-PLA is weighed and added thereto, and the reaction is performed at 100° C. for 12 hours to obtain mPEG-PLA-tocopherol (or cholesterol). The synthesized polymer is dissolved in acetonitrile or methylene chloride, precipitated in hexane/diethyl ether, and filtered.

In the above two preparation processes, tocopherol (or cholesterol) malonate, tocopherol (or cholesterol) glutarate, or tocopherol (or cholesterol) adipate, etc. can be used instead of tocopherol (or cholesterol) succinate.

In another embodiment, tocopherol or cholesterol is bound to the end of mPEG-PLA by using a dichloride compound as a linkage agent. Specifically, tocopherol or cholesterol is weighed and dehydrated by using a vacuum pump at 50° C. Excessive linkage agent is added thereto, and the reaction is performed for 12 hours. After the reaction is completed, the excessively added linkage agent is removed under vacuum at 100° C. Thereto is added weighed mPEG-PLA, and the reaction is performed at 100° C. for 12 hours. The synthesized polymer is dissolved in methylene chloride, and precipitated in hexane/diethyl ether in order to obtain the amphiphilic block copolymer in which tocopherol or cholesterol is bound to PLA via succinic acid diester, i.e. mPEG-PLA-tocopherol or mPEG-PLA-cholesterol. The precipitated polymeric product is filtered, and dried under vacuum to obtain the polymer as white particles. The linkage agent which can be used in the reaction may be selected from such dichloride compounds as succinyl chloride, oxalyl chloride, malonyl chloride, glutaryl chloride, adipoyl chloride, etc.

The block copolymer synthesized as above may be mixed with a poorly water-soluble drug in order to obtain a polymeric micelle composition. That is, the block copolymer (10-200 mg) and the drug (1-50 mg) are dissolved in an organic solvent, e.g. acetonitrile, methylene chloride, etc. The solution is mixed by stirring, and dried under vacuum at 60° C. to prepare a matrix. The matrix of the poorly water-soluble drug and the polymer is dissolved in distilled water, and then lyophilized to obtain the drug-introduced polymeric micelle composition. The above polymeric micelle composition may be diluted with an aqueous solution, e.g. physiological saline, and be used as an injectable formulation.

The term "poorly water-soluble drugs" or "hydrophobic drugs" refers to any drug or bioactive agent which has the water solubility of 33.3 mg/ml or less. This includes anti-cancer agents, antibiotics, anti-inflammatory agents, anesthetics, hormones, antihypertensive agents, and agents for the treatment of diabetes, antihyperlipidemic agents, antiviral agents, agents for the treatment of Parkinson's disease, antidementia agents, antiemetics, immunosuppressants, antiulcerative agents, laxatives, and antimalarial agents. Examples of hydrophobic drugs include paclitaxel, ketoconazole, itraconazole, cyclosporine, cisapride, acetaminophen, aspirin, acetyl salicylic acid, indomethacin, naproxen, wafarin, papaverine, thiabendazole, miconazole, cinarizine, doxorubicin, omeprazole, cholecalciferol, melphalan, nifedipine, digoxin, benzoic acid tryptophan, tyrosine, phenyl alanine, azthreonam, ibuprofen, phenoxymethylpenicillin, thalidomide, methyl testosterone, prochlorperazine, hydrocortisone, dideoxypurine nucleoside, vitamin D2, sulfonamide, sulfonylurea, para-aminobenzoic acid, melatonin, benzyl penicillin, chlorambucil, diazepine, digitoxin, hydrocortisone butyrate, metronidazole benzoate, tolbutamide, prostaglandin, fludrocortisone, griseofulvin, miconazole nitrate, leukotriene B4 inhibitor, propranolol, theophylline, flubiprofen, sodium benzoate, benzoic acid, riboflavin, benzodiazepine, phenobarbital, glyburide, sulfadiazine, sulfaethyl thiadiazole, diclofenac sodium, phenyroin, hioridazine hydrochloride, bropyrimie, hydrochlorothiazide, fluconazole, etc.

The above poorly water-soluble drug may be added to the block copolymer in a weight-by-weight ratio of 0.1-20.0:

80.0-99.9, to be appropriately contained in the inner core of the micelle formed from the amphiphilic block copolymer of the present invention.

In another embodiment, the present invention provides a polymeric composition comprising an amphiphilic block copolymer of a hydrophilic A block and a hydrophobic B block with a terminal hydroxyl group, and a polylactic acid derivative wherein said terminal hydroxyl terminal group of the hydrophobic B block is substituted with a tocopherol or cholesterol group, and at least one end of the polylactic acid derivative is covalently bound to at least one carboxyl group.

The amphiphilic block copolymer comprised of a hydrophilic A block and a hydrophobic B block, wherein the hydroxyl terminal group of the hydrophobic block is substituted with a hydrophobic tocopherol or cholesterol group, which has excellent hydrophobicity, is as described above.

One or more ends of the polylactic acid derivative of the present invention are covalently bound to at least one carboxylic acid or carboxylate salt. The non-bound end of the polylactic acid derivative of the present invention may be covalently bound to a functional group selected from the group consisting of hydroxyl, acetoxy, benzoyloxy, decanoyloxy, and palmitoyloxy. The carboxylic acid or carboxylate salt functions as a hydrophilic group in an aqueous solution of pH 4 or more, and enables the polylactic acid derivative to form polymeric micelles therein. When the polylactic acid derivative of the present invention is dissolved in an aqueous solution, the hydrophilic and hydrophobic components present in the polylactic acid derivative should be balanced in order to form polymeric micelles. Therefore, the number average molecular weight of the polylactic acid derivative of the present invention is preferably within the range of 50 to 50,000 Daltons. The molecular weight of the polylactic acid derivative can be adjusted by controlling the reaction temperature, time, and the like, during the preparation process.

The polylactic acid derivative is preferably represented by the following formula:

$$RO-CHZ-[A]_n-[B]_m-COOM \qquad (I)$$

wherein A is —COO—CHZ—; B is —COO—CHY—, —COO—CH₂CH₂CH₂CH₂CH₂— or —COO—CH₂CH₂OCH₂; R is a hydrogen atom, or acetyl, benzoyl, decanoyl, palmitoyl, methyl, or ethyl group; Z and Y each are a hydrogen atom, or methyl, or phenyl group; M is H, Na, K, or Li; n is an integer from 1 to 30, and m is an integer from 0 to 20.

One or more ends of the polylactic acid derivative of the present invention are covalently bound to a carboxyl group or an alkali metal salt thereof, preferably, an alkali metal salt thereof. The metal ion in the alkali metal salt forms of the polylactic acid derivative is monovalent, e.g. sodium, potassium, or lithium. The polylactic acid derivative in the metal ion salt form is solid at room temperature, and is very stable because of its relatively neutral pH.

More preferably, the polylactic acid derivative is represented by the following formula:

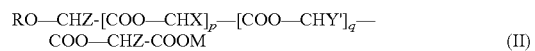

$$RO-CHZ-[COO-CHX]_p-[COO-CHY']_q- \\ COO-CHZ-COOM \qquad (II)$$

wherein X is a methyl group; Y' is a hydrogen atom or phenyl group; p is an integer from 0 to 25; q is an integer from 0 to 25, provided that p+q is an integer from 5 to 25; R, Z and M are each as defined in Formula (I).

In addition, polylactic acid derivatives of the following formulas (III) to (V) are also suitable for the present invention:

$$RO\text{-}PAD\text{-}COO\text{—}W\text{-}M' \qquad (III)$$

wherein W-M' is

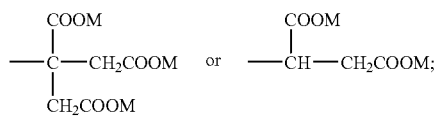

the PAD is a member selected from the group consisting of D,L-polylactic acid, D-polylactic acid, polymandelic acid, a copolymer of D,L-lactic acid and glycolic acid, a copolymer of D,L-lactic acid and mandelic acid, a copolymer of D,L-Lactic acid and caprolactone, and a copolymer of D,L-lactic acid and 1,4-dioxan-2-one; R and M are each as defined in formula (I).

$$S\text{—}O\text{-}PAD\text{-}COO\text{-}Q \qquad (IV)$$

wherein S is

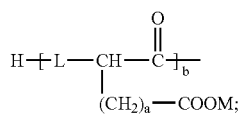

L is $-NR_1-$ or $-O-$; $R_1$ is a hydrogen atom or $C_{1-10}$alkyl; Q is $CH_3$, $CH_2CH_3$, $CH_2CH_2CH_3$, $CH_2CH_2CH_2CH_3$, or $CH_2C_6H_5$; a is an integer from 0 to 4; b is an integer from 1 to 10; M is as defined in Formula (I); and PAD is as defined in formula (III).

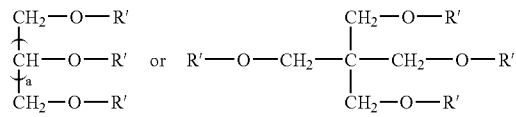

wherein R' is -PAD-O—C(O)—CH$_2$CH$_2$—C(O)—OM and M is as defined in formula (I); PAD is as defined in formula (III); and a is an integer from 1 to 4, for example, if a=1, 3-arm PLA-COONa; if a=2, 4-arm PLA-COONa; if a=3, 5-arm PLA-COONa; and if a=4, 6-arm PLA-COONa.

The initiator for synthesis of the polymers (formula V) includes glycerol, erythritol, threltol, pentaerytritol, xylitol, adonitol, sorbitol, and mannitol.

The polymeric composition of the present invention may contain 0.1 to 99.9 wt % of the amphiphilic block copolymer and 0.1 to 99.9 wt % of the polylactic acid derivative based on the total weight of the amphiphilic block copolymer and the polylactic acid derivative. Preferably, the polymeric composition of the present invention contains 20 to 95 wt % of the amphiphilic block copolymer and 5 to 80 wt % of the polylactic acid derivative. More preferably, the polymeric composition of the present invention contains 50 to 90 wt % of the amphiphilic block copolymer and 10 to 50 wt % of the polylactic acid derivative.

The polylactic acid derivatives of the present invention alone can form micelles in an aqueous solution of pH 4 or more, but the polymeric compositions can form micelles in an aqueous solution irrespective of the pH of the solution. Since the biodegradable polymer is usually hydrolyzed at a pH of 10 or more, the polymeric compositions of the present invention may be used at a pH within the range of 1 to 10, preferably at a pH within the range of 4 to 8. The particle size of the micelles or nanoparticles prepared from the polymeric compositions of the present invention may be adjusted to be within the range of 1 to 400 nm, and preferably from 5 to 200 nm, depending on the molecular weight of the polymers and the ratio of the polylactic acid derivative to the amphiphilic block copolymer.

Figure 2:
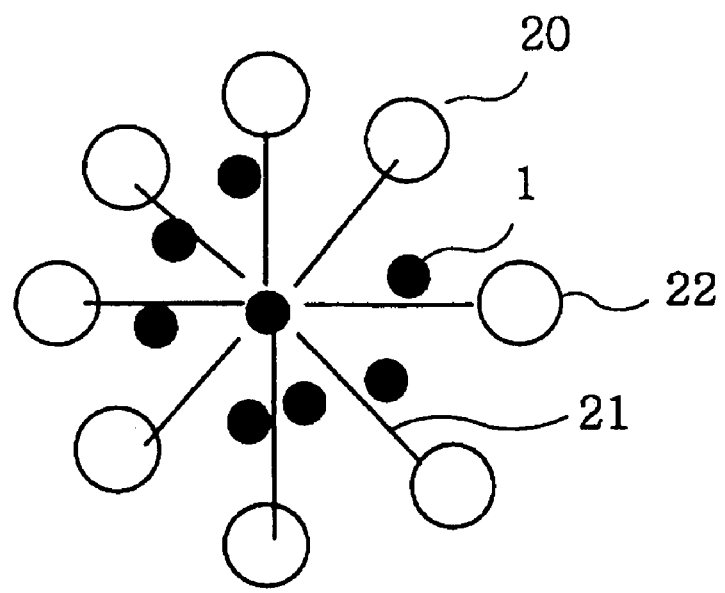
FIG. 2 is a schematic diagram of a polymeric micelle formed by sodium carboxylate derivatized D,L-polylactic acid in an aqueous environment.
Figure 3:
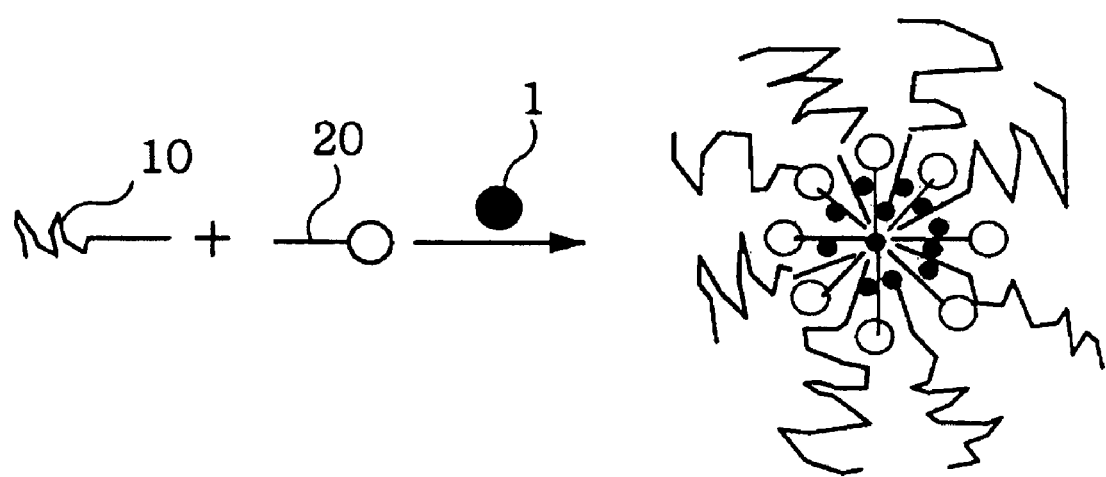
FIG. 3 is a schematic diagram of a polymeric micelle formed by a mixture of monomethoxypolyethylene glycol-polylactide-hydrophobic moiety (mPEG-PLA-hydrophobic moiety) and sodium carboxylate derivatized D,L-polylactic acid in an aqueous environment.

As illustrated in FIG. 1 to FIG. 3, the polylactic acid derivatives or the amphiphilic block copolymers alone and mixtures thereof may form micelles in an aqueous solution, and the micelles formed from the polymeric compositions of the amphiphilic block copolymers and the polylactic acid derivatives in an aqueous solution show higher drug entrapping rates and stability than with those from the polylactic acid derivatives or the amphiphilic block copolymers alone. In the Figures, 1 represents poorly water-soluble drugs; 10 represents monomethoxypolyethylene glycol-polylactide hydrophobic moiety (mPEG-PLA-hydrophobic moiety); 11 represents monomethoxypolyethylene glycol (mPEG); 12 represents polylactide hydrophobic moiety (PLA-hydrophobic moiety); 20 represents the sodium salt of D,L-poly(lactic acid); 21 represents D,L-polylactic acid; and 22 represents sodium carboxylate. However, the polymeric compositions of the present invention remarkably improve the drug loading efficiency and stability of the micelles formed in an aqueous solution compared with the micelles formed from the polylactic acid derivatives or the amphiphilic block copolymers alone.

In one embodiment of the present invention, there is provided a polymeric composition comprising an amphiphilic block copolymer comprised of a hydrophilic A block and a hydrophobic B block with a terminal hydroxyl group and a polylactic acid derivative, wherein said terminal hydroxyl group is substituted with a hydrophobic tocopherol or cholesterol group, and at least one end of the polylactic acid derivative is covalently bound to at least one carboxyl group, wherein said carboxyl group is fixed with a di- or tri-valent metal ion.

The metal ion-fixed polymeric composition can be prepared by adding the di- or tri-valent metal ion to the polymeric composition of the amphiphilic block copolymer and the polylactic acid derivative. The polymeric micelles or nanoparticles may be formed by changing the amount of di- or tri-valent metal ion added for binding or fixing the carboxyl terminal group of the polylactic acid derivative.

The di- or tri-valent metal ion is preferably one selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$, and $Al^{3+}$. The di- or tri-valent metal ion may be added to the polymeric composition of the amphiphilic block copolymer and the polylactic acid derivative in the form of sulfate, chloride, carbonate, phosphate or hydroxylate, and preferably in the form of $CaCl_2$, $MgCl_2$, $ZnCl_2$, $AlCl_3$, $FeCl_3$, $CaCO_3$, $MgCO_3$, $Ca_3(PO_4)_2$, $Mg_3(PO_4)_2$, $AlPO_4$, $MgSO_4$, $Ca(OH)_2$, $Mg(OH)_2$, $Al(OH)_3$, or $Zn(OH)_2$.

Figure 4:
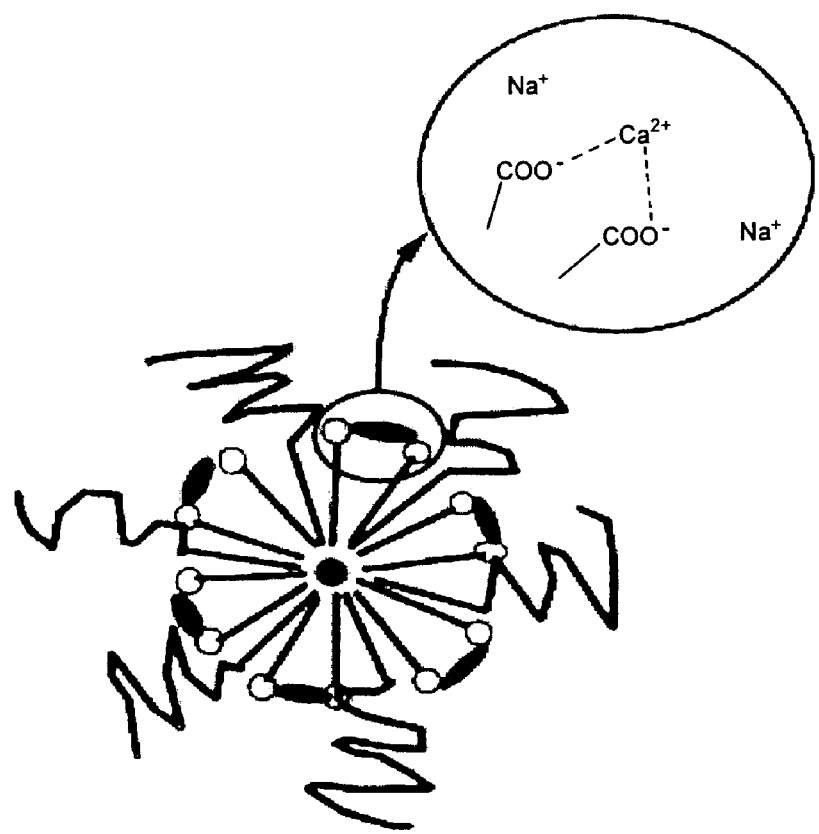
FIG. 4 is a schematic diagram of the $Ca^{2+}$-fixed polymeric micelle of FIG. 3.
Figure 5:
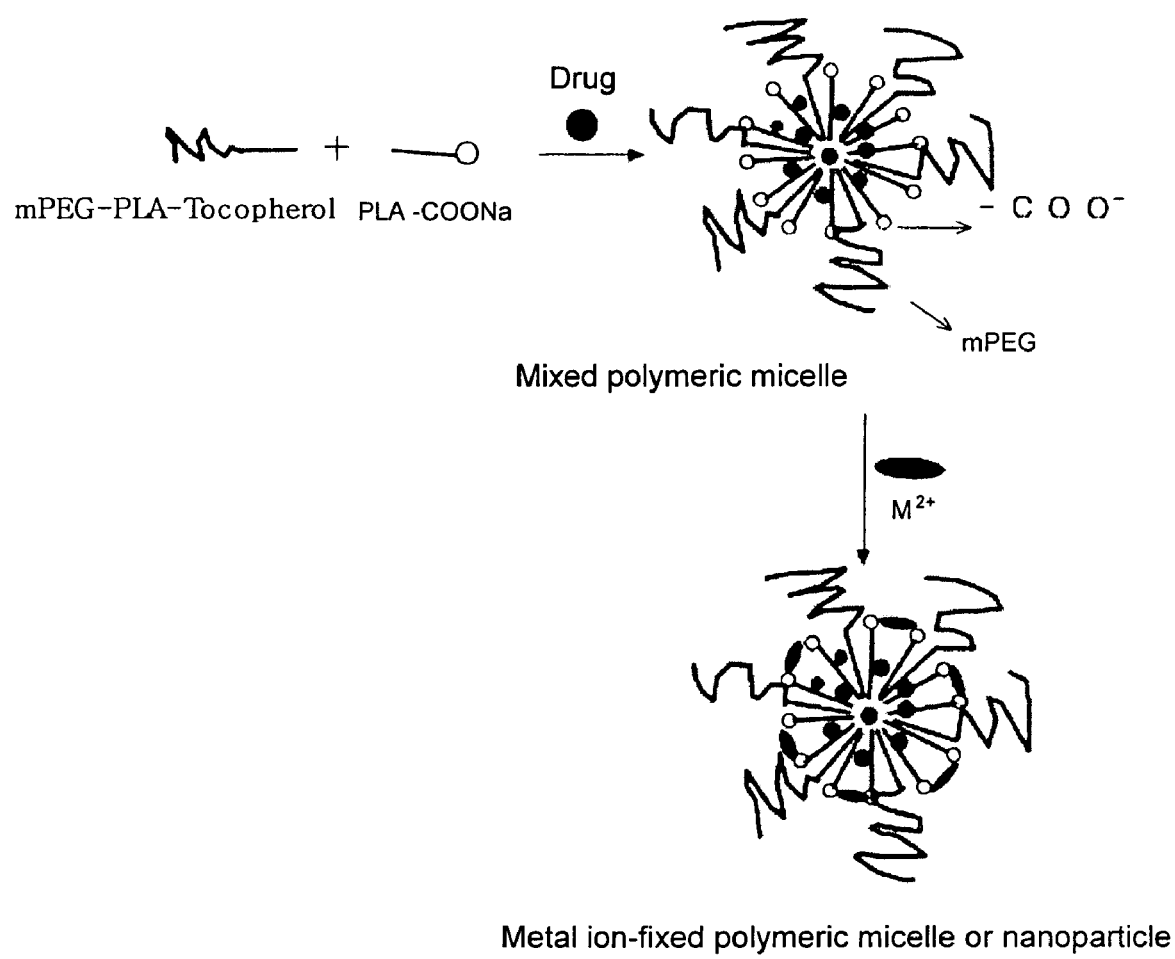
FIG. 5 is a schematic diagram of a $Ca^{2+}$-fixed polymeric micelle containing a hydrophobic drug trapped within the hydrophobic core of the micelle.

As illustrated in FIGS. 4 and 5, when a monovalent metal ion at the carboxyl terminus of the polylactic acid derivative is substituted with a di- or tri-valent metal ion to form a metal ionic bond, the micelles or nanoparticles formed therefrom may have improved stability.

Polymeric micelles or nanoparticles can be prepared by changing the equivalents of the metal ion added. Specifically, if a di-valent metal ion is added at 0.5 equivalents or less with respect to the carboxyl terminal groups of the polylactic acid derivative, the metal ion that can form bonds with the carboxyl terminal group is insufficient, and thus polymeric micelles are formed. If a di-valent metal ion is added at 0.5 equivalents or more, the metal ion that can form bonds with the carboxyl terminal group of the polylactic acid derivative is sufficient to firmly fix the micelles, and thus nanoparticles are formed.

In addition, the drug release rate from the polymeric micelles or nanoparticles may be adjusted by changing the amount of equivalents of the metal ion added. If the metal ion is present at 1 equivalent or less with respect to the carboxyl group of the polylactic acid derivative, the number available for bonding to the carboxyl terminal group of the polylactic acid derivative is decreased, and so the drug release rate is increased. If the metal ion is present at 1 equivalent or more, the number available for bonding to the carboxyl terminal group of the polylactic acid derivative is increased, and so the drug release rate is decreased. Therefore, to increase the drug release rate in the blood, the metal ion is used in a small equivalent amount, and to decrease the drug release rate, the metal ion is used in a large equivalent amount.

The metal ion-fixed polymeric compositions of the present invention may contain 5 to 95 wt % of the amphiphilic block copolymer, 5 to 95 wt % of the polylactic acid derivative, and 0.01 to 10 equivalents of the di- or tri-valent metal ion with respect to the number of equivalents of the carboxyl terminal groups of the polylactic acid derivatives. Preferably, they contain 20 to 80 wt % of the amphiphilic block copolymer, 20 to 80 wt % of the polylactic acid derivative, and 0.1 to 5 equivalents of the di- or tri-valent metal ion. More preferably, they contain 20 to 60 wt % of the amphiphilic block copolymer, 40 to 80 wt % of the polylactic acid derivative, and 0.2 to 2 equivalents of the di- or tri-valent metal ion.

The polymeric composition comprising an amphiphilic block copolymer comprised of a hydrophilic block and a hydrophobic block in which the hydroxyl terminal group is substituted with a hydrophobic tocopherol or cholesterol group having excellent hydrophobicity, and a polylactic acid derivative in which the end of the polylactic acid is covalently bound to at least one carboxyl group, and the metal ion-fixed polymeric composition thereof may form stable polymeric micelles or nanoparticles in an aqueous environment. Therefore, the present invention also relates to a pharmaceutical composition containing polymeric micelles or nanoparticles formed from the polymeric compositions of the present invention with a poorly water-soluble drug entrapped therein. The above composition has a prolonged retention time of effective drug concentration in the bloodstream after administration. The pharmaceutical compositions of the present invention provide increased plasma concentrations of hydrophobic drugs and can be used in various pharmaceutical formulations.

As shown in FIGS. 3 to 5, a poorly water-soluble drug is mixed with a polymeric composition of an amphiphilic block copolymer and a polylactic acid derivative to form polymeric micelles containing the drug therein. A di- or tri-valent metal ion may be added to form a metal ionic bond with the carboxyl terminal group of the polylactic acid derivative and thereby to form drug-containing polymeric micelles and nanoparticles with increased stability.

The content of the poorly water-soluble drug is preferably within the range of 0.1 to 30 wt % based on the total weight of the pharmaceutical compositions comprising an amphiphilic block copolymer, a polylactic acid derivative, and a hydrophobic drug. The size of the drug-containing polymeric micelles or nanoparticles may be adjusted from 5 to 400 nm, preferably, from 10 to 200 nm, depending on the molecular weight of the polymers and the ratio of the amphiphilic block copolymer to the polylactic acid derivative. For an example, the particles of the metal ion-fixed polymeric micelles or nanoparticles have an average size of 20-40 nm, as shown in Table 7. The micelles of this size range are suitable for injection formulations and sterile filtration.

The non-metal ion-treated polymeric composition or metal ion-fixed polymeric micelles or nanoparticles according to the present invention have high stability, and particularly, the metal ion-fixed ones have much higher stability in an aqueous solution. As shown in Table 9, the drug containing polymeric micelle compositions (Compositions 4 & 5) were kinetically stable and the metal ion-fixed paclitaxel-containing polymeric micelle composition were even more kinetically stable. The addition of a metal ion can significantly increase the retention time of drug in the polymeric micelles of the present invention. This is due to the crosslinking electrostatic interaction of the carboxylate anion of the polylactic acid derivative which might induce an increase in the rigidity of the hydrophobic core.

Moreover, the metal ion-fixed polymeric micelles (Composition 4) of the amphiphilic diblock copolymers with a hydrophobic moiety (tocopherol succinic acid) substituted for the hydroxyl terminal group of the hydrophobic B block kinetically had greater stability than the original mPEG-PLA-OH (Composition 7). This result suggests that the increase of hydrophobicity of hydrophobic B block in the amphiphilic polymer results in the formation of more stable micelles due to stronger interactions between the hydrophobic moiety of the amphiphilic polymer and drug.

Figure 9:
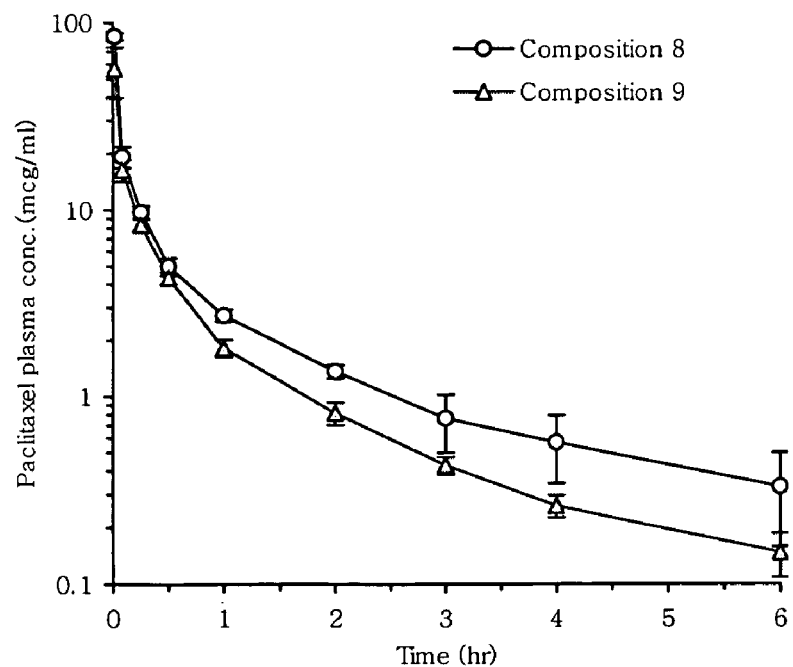
FIG. 9 shows the plasma drug concentration of paclitaxel-containing $Ca^{2+}$-fixed polymeric micelles fabricated with mPEG-PLA-tocopherol and mPEG-PLA-OH at various time intervals after administration.

The metal ion-fixed polymeric micelles (Composition 8) of the amphiphilic diblock copolymers with a hydrophobic moiety (tocopherol succinic acid) substituted for the hydroxyl terminal group of the hydrophobic B block has a much longer bloodstream retention time than the metal ion-fixed polymeric micelles (Composition 9) of the original amphiphilic diblock copolymer as shown in Table 11 and FIG. 9. This result also suggests, as demonstrated in Example 36, that the increase of hydrophobicity of the hydrophobic B block in the amphiphilic polymer results in the formation of more stable micelles due to stronger interactions between the hydrophobic moiety of the amphiphilic polymer and drug.

As shown in FIGS. 10-13, a composition, wherein the drug is entrapped in the metal ion-fixed polymeric composition has a longer retention time of drug in the bloodstream, and so maintains an effective plasma drug concentration for a longer period of time as compared with the currently marketed formulations.

The present invention also provides a pharmaceutical composition for use as an anticancer agent. In a preferable embodiment, it provides a pharmaceutical composition for use as an anticancer agent, comprising an amphiphilic block copolymer of a hydrophilic A block and a hydrophobic B block with a terminal hydroxyl group, and a polylactic acid derivative, wherein said terminal hydroxyl terminal group of the hydrophobic B block is substituted with a tocopherol or cholesterol group, and at least one end of the polylactic acid derivative is covalently bound to at least one carboxyl group, and an anticancer drug. The carboxyl terminal group of the polylactic acid derivative can be further fixed with a di- or tri-valent metal ion.

Examples of the anticancer drugs include, but are not limited to, taxoids, taxines or taxanes like paclitaxel and docetaxel; phodophyllotoxins; camptothecins like camptothecin, 9-nitrocamptothecin, 9-aminocamptothecin, camptothecin-11, topodecane; anthracyclines like doxorubicin, epirubicin, aclarubicin, idarubicin, pyrarubicin; vinca alkaloids like vincristine, vinorelbine, vindesine, vintripole, vinsaltine; eposilones, platinum, etoposide, methotrexate, carmustine, 5-fluorouracil, retinoic acid, retinol, tamoxifen, mitomycin B, mitomycin C, amonafide, illudin S, etc.

Figure 15:
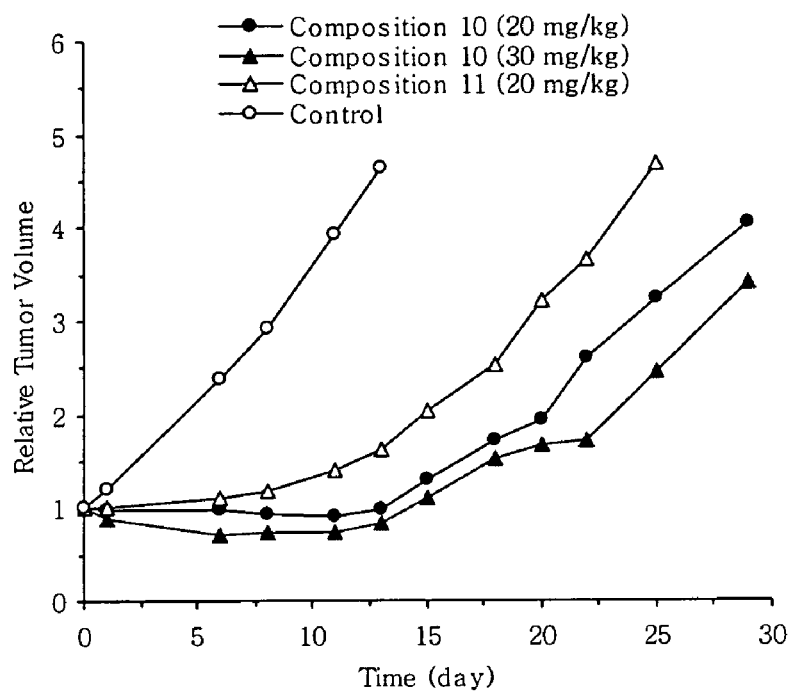
FIG. 15 shows the anticancer effects of the drug containing $Ca^{2+}$-fixed polymeric micelles in the animal model with paclitaxel (Taxol®) resistant human cancer.
Figure 16:
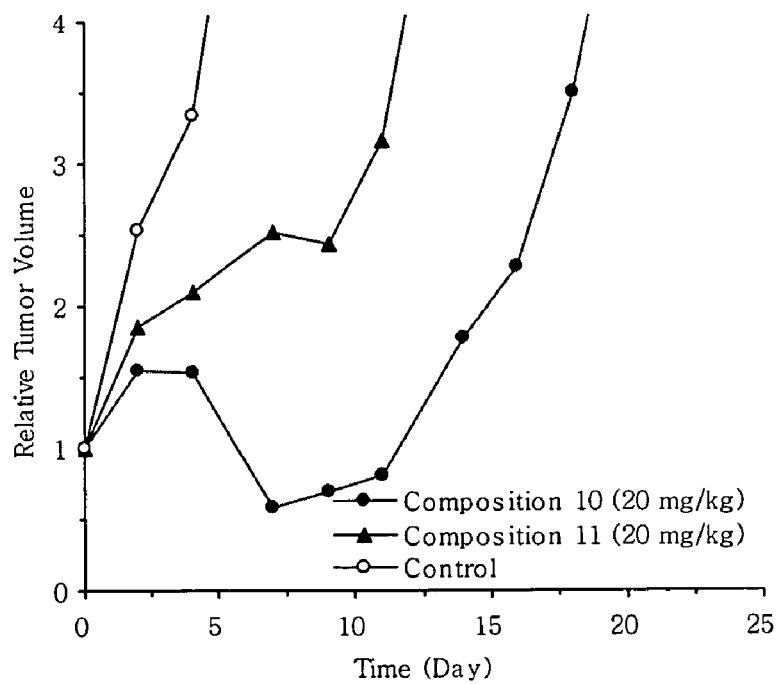
FIG. 16 shows the anticancer effects of the drug containing $Ca^{2+}$-fixed polymeric micelles in an animal model with doxorubicin (Adriamycin®) resistant human cancer.

The polymeric micelle-pharmaceutical composition obtained has greatly improved pharmaceutical efficacy. As a specific example, as shown in FIGS. 14A-H, paclitaxel containing $Ca^{2+}$-fixed polymeric micelles has a high inhibition rate on cancer growth, and also inhibits the growth of anticancer drug-resistant cancer cells (FIGS. 15 & 16).

Figure 10:
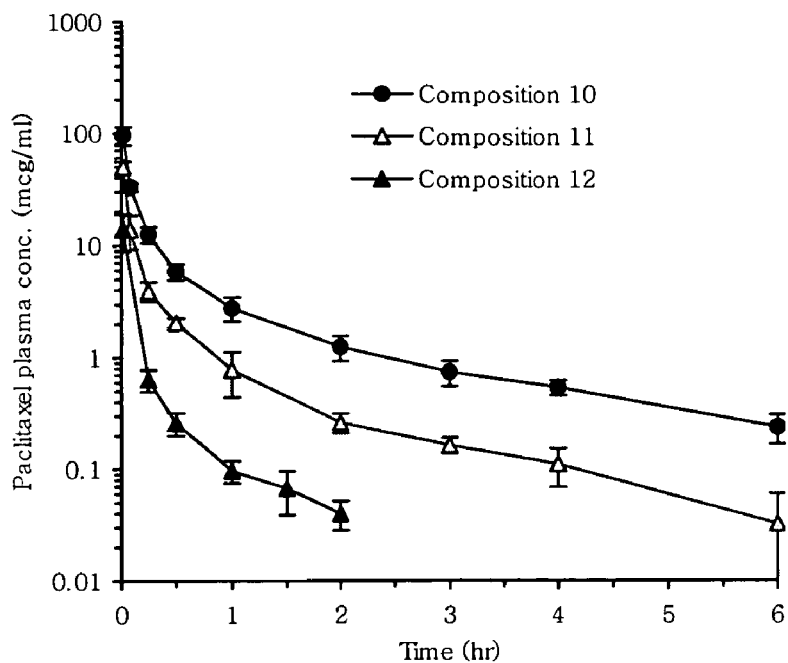
FIG. 10 shows the profile of plasma drug concentration of paclitaxel-containing $Ca^{2+}$-fixed polymeric micelles, Cremophor EL (Taxol®), and Tween 80 preparations at various time intervals after administration.

Taxol® (or paclitaxel), doxorubicin, etc. are widely used in chemotherapeutic treatment of cancer. These anticancer drugs are effective and useful in chemotherapy, but the development of anticancer drug-resistance in cancer cells always renders the drugs ineffective. Various mechanisms of Taxol®-resistance including the overexpression of P-glycoprotein (P-gp) and modification of β-tubulin have been characterized. Among them, the overexpression of P-gp has been a predominant mechanism to explain the multi-drug resistant phenomena, including Taxol®-resistance. Anticancer drug-resistant cancer cells show higher $IC_{50}$ (50% cell inhibition concentration of drug) than normal ones, and so chemotherapy with the anticancer drug requires a higher concentration of drug in the tumor cells. Therefore, specific localization of the drug in the tumor tissue is required for guaranteeing effectiveness. The metal ion fixed polymeric micelle had a longer circulation time than the conventional formulations as shown in FIG. 10. Thus, it accumulated more selectively in the tumor tissue by an enhanced permeation and retention (EPR) effect compared to the conventional formulations. To demonstrate the effectiveness of metal ion-fixed polymeric micelles against anticancer drug-resistant cancer, an animal model for in vivo anti-cancer activity against Taxol®-resistant cancer was established. When the cancer cells which had been inoculated into mice were exposed repeatedly to Taxol®, the $IC_{50}$ of the drug for Taxol®-pretreated cancer cells was increased significantly compared to that of the drug for the native cancer cells. In this animal model, the metal ion-fixed polymeric micelle (Composition 10) treated group showed a higher inhibition rate than the Cremophor EL formulation (Composition 11) treated group, possibly due to the longer retention time for an effective concentration of the drug incorporated in the metal ion-fixed polymeric micelle as shown in FIG. 15 and Table 22. The same effect could be obtained from the doxorubicin-resistant cancer animal model (FIG. 16).

Therefore, the present invention provides a method for treating a drug-resistant cancer comprising administering an effective amount of the pharmaceutical composition of the present invention to a warm-blooded animal in need of said treatment.

Furthermore, the present invention includes a process for preparing the above pharmaceutical composition. Specifically, as shown in FIGS. 3 and 5, the polylactic acid derivative, the amphiphilic block copolymer, and the poorly water-soluble drug at a certain ratio can be dissolved in one or more solvents selected from the group consisting of acetone, ethanol, methanol, ethyl acetate, acetonitrile, methylene chloride, chloroform, acetic acid, and dioxane. The organic solvent can be removed therefrom to prepare a homogenous mixture of the poorly water-soluble drug and the polymer. The homogenous mixture of the poorly water-soluble drug and the polymeric composition of the present invention can be added to an aqueous solution of pH 4 to 8, at 0 to 80° C. resulting in a poorly water-soluble drug-containing mixed polymeric micelle aqueous solution. The above drug-containing polymeric micelle aqueous solution can then be lyophilized to prepare the polymeric micelle composition in a solid form.

An aqueous solution containing 0.001 to 2 M of the di- or tri-valent metal ion is added to the poorly water-soluble drug-containing mixed polymeric micelle aqueous solution to form metal ion-fixed polymeric micelles. The mixture is slowly stirred at room temperature for 0.1 to 1 hour, and then lyophilized to prepare the metal ion-fixed polymeric micelle or nanoparticle composition in a solid form.

Polymeric micelles or nanoparticles of the present invention wherein poorly water-soluble drug is entrapped and solubilized can be administered orally or parenterally. The drug is released from the hydrophobic core of the micelles to exhibit a pharmacological effect while the micelles are degraded. Particularly, the metal ion-fixed polymeric micelles or nanoparticles are retained in the bloodstream for a long period of time, and accumulate in the target lesions.

For parenteral delivery, polymeric micelles or nanoparticles may be administered intravenously, intramuscularly, intraperitoneally, transnasally, intrarectally, intraocularly, or intrapulmonarily. For oral delivery, the drug is mixed with the polymeric micelles of the present invention, and then administered in the form of tablet, capsule, or aqueous solution.

The dose of the polymeric micelles or nanoparticles used in the present invention can be changed over a wide range according to various conditions such as patient's symptoms, age and body weight, and the like.

The following examples will enable those skilled in the art to more clearly understand how to practice the present invention. It should be understood that though the invention has been described in conjunction with the preferred specific embodiments thereof, the following is not intended to limit the scope of the present invention. Other aspects of the invention will be apparent to those skilled in the art to which the invention pertains.

PREPARATION EXAMPLE 1

Synthesis 1 of D,L-polylactic Acid (PLA-COOH)

One hundred grams of D,L-lactic acid were introduced into a 250 ml three-neck round-bottomed flask. The flask was equipped with a stirrer, and heated in an oil bath to 80° C. The reaction was performed for 1 hour under the pressure reduced to 25 mmHg by a vacuum aspirator to remove excessive moisture. The reaction was then performed at a temperature of 150° C. under a reduced pressure of 25 mmHg for 6 hours. The resulting product was added to 1 liter of distilled water to precipitate the polymer. The precipitated polymer was then added to distilled water to remove the low molecular weight polymer that was soluble in an aqueous solution with a pH of 4 or less. The precipitated polymer was then added to 1 liter of distilled water, and the pH of the aqueous solution was adjusted to 6 to 8 by the addition of sodium hydrogen carbonate portionwise thereto to dissolve the polymer. The water-insoluble polymer was separated and removed by centrifugation or filtration. A 1 N hydrochloric acid solution was added dropwise thereto and the polymer was precipitated in the aqueous solution. The precipitated polymer was washed twice with distilled water, isolated and dried under reduced pressure to obtain a highly viscous liquid (78 g of D,L-polylactic acid, yield: 78%). The number average molecular weight of the polymer was 540 Daltons as determined by $^1$H-NMR spectrum.

PREPARATION EXAMPLES 2 to 4

Synthesis 2 of D,L-polylactic Acid (PLA-COOH)

D,L-polylactic acid was obtained according to the same procedure as in Preparation Example 1 except for the control of the reaction temperature, pressure, and time as set forth in Table 1. The number average molecular weight and the yield of D,L-polylactic acid synthesized from the above Preparation Examples 1 to 4 are shown in the following Table 1.

TABLE 1

| Preparation Example | Temperature (° C.) | Time (hours) | Pressure (mmHg) | Mn | Yield (%) |
|---|---|---|---|---|---|
| 1 | 150 | 6 | 25 | 540 | 78 |
| 2 | 160 | 12 | 10 | 1140 | 83 |
| 3 | 160 | 24 | 10 | 1550 | 84 |
| 4 | 160 | 24 | 5 | 2100 | 87 |

* Yield = (Obtained polymer/Used monomer) × 100

PREPARATION EXAMPLE 5

Synthesis 1 of the Copolymer of D,L-lactic Acid and Glycolic Acid (PLGA-COOH)

Fifty-five (55) grams of D,L-lactic acid (0.6 moles) and 45 grams of glycolic acid (0.6 moles) were introduced together into a 250 ml three-neck round-bottomed flask. The same procedure as in Preparation Example 1 was carried out except that the reaction was performed at a temperature of 150° C. and under a reduced pressure of 10 mmHg for 12 hours.

PREPARATION EXAMPLE 6

Synthesis 2 of the Copolymer of D,L-lactic Acid and Glycolic Acid (PLGA-COOH)

Seventy-three (73) grams of D,L-lactic acid (0.8 moles) and 27 grams of glycolic acid (0.35 moles) were introduced together into a 250 ml three-neck round-bottomed flask. The same procedure as in Preparation Example 1 was carried out except that the reaction was performed at a temperature of 160° C. and under a reduced pressure of 10 mmHg for 12 hours.

PREPARATION EXAMPLE 7

Synthesis 3 of the Copolymer of D,L-lactic Acid and Glycolic Acid (PLGA-COOH)

Ninety-one (91) grams of D,L-lactic acid (1.0 mole) and 9 grams of glycolic acid (0.12 moles) were introduced together into a 250 ml three-neck round-bottomed flask. The same procedure as in Preparation Example 1 was carried out except that the reaction was performed at a temperature of 160° C. and under a reduced pressure of 10 mmHg for 12 hours.

PREPARATION EXAMPLE 8

Synthesis 4 of the Copolymer of D,L-lactic Acid and Glycolic Acid (PLGA-COOH)

Seventy-three (73) grams of D,L-lactic acid (0.8 moles) and 27 grams of glycolic acid (0.35 moles) were introduced into a 250 ml three-neck round-bottomed flask. The same procedure as in Preparation Example 1 was carried out except that the reaction was performed at a temperature of 180° C. and under a reduced pressure of 5 mmHg for 24 hours.

The copolymers synthesized in the above Preparation Examples 5 to 8 are shown in Table 2.

TABLE 2

| Preparation Example | Molar ratio of lactic acid and glycolic acid | | Reaction temperature (° C.) | Reaction time (hrs) | Pressure (mmHg) | Mn | Yield (%) |
|---|---|---|---|---|---|---|---|
| | Reactant | Product | | | | | |
| 5 | 50/50 | 52/48 | 150 | 12 | 10 | 920 | 63 |
| 6 | 70/30 | 67/33 | 160 | 12 | 10 | 1040 | 65 |
| 7 | 90/10 | 91/9 | 160 | 12 | 10 | 1180 | 68 |
| 8 | 70/30 | 71/29 | 180 | 24 | 5 | 1650 | 73 |

PREPARATION EXAMPLE 9

Synthesis of a Copolymer of D,L-lactic Acid and Mandelic Acid (PLMA-COOH)

Seventy-five (75) grams of D, L-lactic acid (0.83 moles) and 25 grams of D,L-mandelic acid (0.16 moles) were introduced together into a 250 ml three-neck round-bottomed flask. The same procedure as in Preparation Example 1 was carried out except that the reaction was performed at a temperature of 180° C. and under a reduced pressure of 10 to 20 mmHg for 5 hours. Fifty-four (54) g (yield: 54%) of a copolymer of D,L-lactic acid and mandelic acid were obtained. The molar ratio of D,L-lactic acid to mandelic acid was 85/15. The number average molecular weight of the polymer was 1,096 Daltons as determined by $^1$H-NMR spectrum.

PREPARATION EXAMPLE 10

Synthesis of an Acetoxy D,L-polylactic Acid Derivative (AcO-PLA-COOH)

Fifty (50) g of D,L-polylactic acid (Mn: 1,140 Daltons), synthesized from Preparation Example 2, and 20 ml of chloracetic acid were introduced together into a 250 ml round-bottomed flask. The flask was equipped with a refrigerator, and the reaction mixture was refluxed under nitrogen flow for 4 hours. Excessive chloracetic acid was removed by distillation, and the reaction product was added to a mixture of ice and water. The whole mixture was stirred slowly to precipitate the polymer. The precipitated polymer was separated, washed twice with distilled water, and then dissolved in anhydrous acetone. Anhydrous magnesium sulfate was added thereto to remove excessive moisture. The product obtained was filtered to remove the magnesium sulfate. Acetone was removed using a vacuum evaporator, thereby to obtaining liquid acetoxy D,L-polylactic acid (46 g, yield: 92%). By $^1$H-NMR, the acetoxy group was identified as a single peak at 2.02 ppm.

PREPARATION EXAMPLE 11

Synthesis of a Palmitoyloxy D,L-polylactic Acid Derivative (PalmO-PLA-COOH)

Twenty (20) grams of D,L-polylactic acid (Mn: 1,140 Daltons), synthesized from Preparation Example 2, was introduced into a 250 ml round-bottomed flask. The reactant was completely dehydrated under vacuum in an oil bath at 120° C. The oil bath was cooled to 50° C. and 50 ml of acetone was added thereto to completely dissolve the polymer. Five (5) ml of chloropalmitic acid was added thereto, and the reaction was performed at a temperature of 50° C. for 10 hours under nitrogen. The reaction product was washed with an excessive amount of hexane to remove any residual reactant. The product was then dissolved in acetone, and the solution was added to a mixture of ice and water. The whole mixture was stirred slowly resulting in the precipitation of an oligomer. The oligomer was separated and washed twice with distilled water, and then dissolved in anhydrous acetone. Anhydrous magnesium sulfate was added to the solution to remove excessive moisture. The product obtained was filtered to remove the magnesium sulfate. Acetone was removed with a vacuum evaporator, thereby obtaining a palmitoyloxy D,L-polylactic acid derivative (19.1 g, yield: 96%). By $^1$H-NMR, the palmitoyl group was identified as the peaks of 0.88, 1.3, and 2.38 ppm.

PREPARATION EXAMPLE 12

Synthesis of 3arm Polylactic Acid (3arm PLA-COOH)

One (1) gram of glycerol (0.011 mol) was introduced into a 100 ml three-neck round-bottomed flask. The flask was equipped with a stirrer, and heated in an oil bath to 80° C. The reaction was performed for 30 min with the pressure reduced to 25 mmHg by a vacuum aspirator to remove excessive moisture. A reaction catalyst, tin octoate (Tin (Oct) 2), dissolved in toluene was added to the glycerol. The reaction mixture was stirred for 30 minutes, and the pressure was reduced to 1 mmHg at 110° C. for 1 hour to remove the solvent (toluene) dissolving the catalyst. Purified lactide (35.8 g, 0.249 mol; 10 wt %) was added thereto, and the mixture was heated to 130° C. under a reduced pressure of 25 mmHg for 6 hours. The polymer formed was dissolved in acetone, and 0.2 N NaHCO$_3$ aqueous solution was added dropwise thereto to precipitate the polymer. The precipitated polymer was washed three or four times with distilled water, isolated and dried under reduced pressure to obtain a powder (3arm PLA-OH).

One hundred (100) grams of 3arm PLA-OH (0.033 mol) were introduced into a 100 ml one-neck round-bottomed flask. The reaction was performed for 30 min with the pressure reduced to 25 mmHg by a vacuum aspirator to remove excessive moisture. 19.8 grams of succinic anhydride (0.198 mol) were added thereto, and the mixture was heated to 125° C. for 6 hours. The polymer formed was dissolved in acetone, and distilled water was added dropwise thereto to precipitate the polymer. The precipitated polymer was dissolved in a 0.2N NaHCO$_3$ aqueous solution at 60° C. The undissolved polymer was removed by filtration. A 2N HCl aqueous solution was added dropwise thereto to precipitate the polymer. The precipitated polymer was washed five or six times with distilled water, isolated and dried under reduced pressure to obtain a powder (3arm PLA-COOH). The number average molecular weight of the polymer was 3,000 Daltons as determined by $^1$H-NMR spectrum.

PREPARATION EXAMPLE 13

Synthesis of 5arm Polylactic Acid (5arm PLA-COOH)

One (1) gram of xylitol (0.0066 mol) was introduced into a 100 ml three-neck round-bottomed flask. The flask was equipped with a stirrer, and heated in an oil bath to 80° C. The reaction was performed for 30 min with the pressure reduced to 25 mmHg by a vacuum aspirator to remove excessive moisture. A reaction catalyst, tin octoate (Tin (Oct) 2), dissolved in toluene was added into the glycerol. The reaction mixture was stirred for 30 minutes, and the pressure was reduced to 1 mmHg at 110° C. for 1 hour to remove the solvent (toluene) dissolving the catalyst. Purified lactide (31.7 g, 0.151 mol; 10 wt %) was added thereto, and the mixture was heated to 130° C. under the reduced pressure of 25 mmHg for 6 hours. The polymer formed was dissolved in acetone, and 0.2 N NaHCO$_3$ aqueous solution was added dropwise thereto to precipitate the polymer. The precipitated polymer was washed three or four times with distilled water, isolated and dried under reduced pressure to obtain powder (5arm PLA-OH).

One hundred (100) grams of 5arm PLA-OH (0.033 mol) were introduced into a 100 ml one-neck round-bottomed flask. The reaction was performed for 30 min under the pressure reduced to 25 mmHg by a vacuum aspirator to remove excessive moisture. Thirty-three (33.0) grams of succinic anhydride (0.33 mol) were added thereto, and the mixture was heated to 125° C. for 6 hours. The polymer formed was dissolved in acetone, and distilled water was added dropwise thereto to precipitate the polymer. The precipitated polymer was dissolved in 0.2 N NaHCO$_3$ aqueous solution at 60° C. The undissolved polymer was removed by filtration. A 2 N HCl aqueous solution was added dropwise thereto to precipitate the polymer. The precipitated polymer was washed five or six times with distilled water, isolated and dried under reduced pressure to obtain a powder (3arm PLA-COOH). The number average molecular weight of the polymer was 3,000 Daltons as determined by $^1$H-NMR spectrum.

PREPARATION EXAMPLE 14

Synthesis 1 of Sodium Salt of Polylactic Acid (PLA-COONa)

D,L-polylactic acid (Mn: 540 Daltons) synthesized from Preparation Example 1 was dissolved in acetone. The solution was introduced into a round-bottomed flask, and the flask was equipped with a stirrer. The solution was stirred slowly at room temperature, and a sodium hydrogen carbonate solution (1 N) was slowly added thereto to reach a pH of 7. Anhydrous magnesium sulfate was added thereto, and excessive moisture was removed therefrom. The mixture obtained was filtered, and the acetone was evaporated with a solvent evaporator. A white solid was obtained therefrom. The solid was dissolved in anhydrous acetone, and the solution was filtered to remove the insoluble portion. Acetone was evaporated leaving the sodium salt of D,L-polylactic acid (yield: 96%) in a white solid. As shown in FIG. 2, a hydrogen peak adjacent to the carboxylic acid group was observed at 4.88 ppm by $^1$H-NMR, and the polymer when dissolved in water had a pH of 6.5 to 7.5.

PREPARATION EXAMPLE 15

Synthesis 2 of the Sodium Salt of Polylactic Acid (PLA-COONa)

The sodium salt of polylactic acid (yield: 95%) was synthesized according to the same procedure as in the above Preparation Example 14 except that D,L-polylactic acid (Mn: 1,140 Daltons) synthesized from Preparation Example 2 and an aqueous solution of sodium carbonate were used.

PREPARATION EXAMPLE 16

Synthesis of the Sodium Salt of Acetoxy-D,L-polylactic Acid (AcO-PLA-COONa)

The sodium salt of acetoxy-D,L-polylactic acid (yield: 95%) was synthesized according to the same procedure as in Preparation Example 14 except that acetoxy-D,L-polylactic acid (Mn: 1,140 Daltons) synthesized from Preparation Example 10 and an aqueous solution of sodium carbonate were used.

PREPARATION EXAMPLE 17

Synthesis 1 of the Sodium Salt of Palmitoyloxy D,L-polylactic Acid (PalmO-PLA-COONa)

The palmitoyloxy D,L-polylactic acid (Mn: 1,140 Daltons) synthesized from Preparation Example 11 was completely dissolved in an aqueous solution of acetone (28.6 v/v %). The solution was introduced into a round-bottomed flask, and the flask was equipped with a stirrer. The solution was stirred slowly at room temperature, and then an aqueous solution of sodium hydrogen carbonate (1 N) was added thereto for nutralization. The solution was stirred slowly at room temperature and a sodium hydrogen carbonate solution (1 N) was slowly added thereto to reach a pH of 7. Anhydrous magnesium sulfate was added thereto to remove excess moisture. The solution obtained was filtered, and the acetone solution was evaporated with a solvent evaporator. A white solid was obtained therefrom. The solid was dissolved in acetone and the solution was filtered to remove any insoluble particles. The acetone was evaporated and the sodium salt of palmitoyloxy D,L-polylactic acid was obtained as a white solid (yield: 96%).

PREPARATION EXAMPLE 18

Synthesis of the Potassium Salt of Polylactic Acid (PLA-COOK)

The potassium salt of polylactic acid (yield: 98%) was synthesized according to the same procedure as Preparation Example 14 except that D,L-lactic acid (Mn: 1,550 Daltons) synthesized from Preparation Example 3 and an aqueous solution of potassium hydrogen carbonate were used.

PREPARATION EXAMPLE 19

Synthesis 3 of the Sodium Salt of Polylactic Acid (PLA-COONa)

The sodium salt of polylactic acid (yield: 95%) was synthesized according to the same procedure as in Preparation Example 14 except that D,L-lactic acid (Mn: 2,100 Daltons) synthesized from Preparation Example 4 was used.

PREPARATION EXAMPLE 20

Synthesis 1 of the Sodium Salt of a Copolymer of D,L-lactic Acid and glycolic acid (PLGA-COONa)

The sodium salt of a copolymer of D,L-lactic acid and glycolic acid (yield: 98%) was synthesized according to the same procedure as in Preparation Example 14 except that a copolymer of D,L-lactic acid and glycolic acid (Mn: 920 Daltons) synthesized from Preparation Example 5 and an aqueous solution of sodium carbonate were used.

PREPARATION EXAMPLE 21

Synthesis 2 of the Sodium Salt of a Copolymer of D,L-lactic Acid and Glycolic Acid (PLGA-COONa)

The sodium salt of a copolymer of D,L-lactic acid and glycolic acid (yield: 93%) was synthesized according to the same procedure as in Preparation Example 14 except that a copolymer of D,L-lactic acid and glycolic acid (Mn: 1,040 Daltons) synthesized from Preparation Example 6 was used.

PREPARATION EXAMPLE 22

Synthesis of the Potassium Salt of a Copolymer of D,L-lactic Acid and Glycolic Acid (PLGA-COOK)

The potassium salt of a copolymer of D,L-lactic acid and glycolic acid (yield: 92%) was synthesized according to the same procedure as in Preparation Example 14 except that a copolymer of D,L-lactic acid and glycolic acid (Mn: 1,180 Daltons) synthesized from Preparation Example 7 and an aqueous solution of potassium carbonate were used.

PREPARATION EXAMPLE 23

Synthesis 3 of the Sodium Salt of a Copolymer of D,L-lactic Acid and Glycolic Acid (PLGA-COONa)

The sodium salt of a copolymer of D,L-lactic acid and glycolic acid (yield: 98%) was synthesized according to the same procedure as in Preparation Example 14 except that the copolymer of D,L-lactic acid and glycolic acid (Mn: 1,650 Daltons) synthesized from Preparation Example 8 was used.

PREPARATION EXAMPLE 24

Synthesis of the Sodium Salt of a Copolymer of D,L-lactic Acid and Mandelic Acid (PLMA-COONa)

The sodium salt of a copolymer of D,L-lactic acid and mandelic acid (yield: 96%) was synthesized as white solid according to the same procedure as in Preparation Example 14 except that the copolymer of D,L-lactic acid and mandelic acid synthesized from Preparation Example 9 (Mn: 1,096 Daltons) was used.

PREPARATION EXAMPLE 25

Synthesis of the Sodium Salt of 3arm Polylactic Acid (3arm PLA-COONa)

The sodium salt of 3 arm polylactic acid was synthesized as a white solid according to the same procedure as in Preparation Example 14 except that the copolymer of 3-arm D,L-lactic acid (Mn: 3,000 Daltons) synthesized from Preparation Example 12 was used.

PREPARATION EXAMPLE 26

Synthesis of the Sodium Salt of 5arm Polylactic Acid (5arm PLA-COONa)

The sodium salt of 5 arm polylactic acid was synthesized as a white solid according to the same procedure as in Preparation Example 14 except that the copolymer of 5-arm D,L-lactic acid (Mn: 3,000 Daltons) synthesized from Preparation Example 13 was used.

The carboxylate salts of the polylactic acid derivatives synthesized from the above Preparation Examples 14 to 26 are shown in Table 3.

oven for 48 hours. The mPEG-PLA obtained had a number average molecular weight of 2,000-1,765 Daltons, and was confirmed to be of the AB type by $^1$H-NMR.

PREPARATION EXAMPLE 28

Polymerization of a Monomethoxypolyethylene glycol-poly(lactic-co-glycolide) (mPEG-PLGA) Block Copolymer (AB Type)

To synthesize an mPEG-PLGA block copolymer, monomethoxypolyethylene glycol (Mn: 5,000 Daltons) was reacted with lactide and glycolide in the presence of the catalyst stannous octoate, at 120° C. for 12 hours according to the same procedure as in Preparation Example 27. The mPEG-PLGA obtained had a number average molecular weight of 5,000-4,000 Daltons, and was confirmed to be of the AB type by $^1$H-NMR.

PREPARATION EXAMPLE 29

Polymerization of a Monomethoxypolyethylene glycol-poly(lactic-co-p-dioxan-2-one) (mPEG-PLDO) Block Copolymer (AB Type)

To synthesize an mPEG-PLDO block copolymer, monomethoxypolyethylene glycol (Mn: 12,000 Daltons) was reacted with lactide and p-dioxan-2-one in the presence

TABLE 3

| Preparation Example | Reactant (Mn) | Base | Product | Mn (Daltons) | Yield (%) |
|---|---|---|---|---|---|
| 14 | PLA-COOH (540) | NaHCO$_3$ | PLA-COONa | 540 | 96 |
| 15 | PLA-COOH (1,140) | Na$_2$CO$_3$ | PLA-COONa | 1,140 | 95 |
| 16 | AcO-PLA-COOH (1,140) | Na$_2$CO$_3$ | AcO-PLA-COONa | 1,140 | 95 |
| 17 | PalmitoylO-PLA-COOH (1,140) | NaHCO$_3$ | PalmitoylO-PLA-COONa | 1,140 | 96 |
| 18 | PLA-COOH (1,550) | KHCO$_3$ | PLA-COOK | 1,550 | 98 |
| 19 | PLA-COOH (2,100) | NaHCO$_3$ | PLA-COONa | 2,100 | 95 |
| 20 | PLGA-COOH (920) | Na$_2$CO$_3$ | PLGA-COONa | 920 | 98 |
| 21 | PLGA-COOH (1,040) | NaHCO$_3$ | PLGA-COONa | 1,040 | 93 |
| 22 | PLGA-COOH (1,180) | K$_2$CO$_3$ | PLGA-COOK | 1,180 | 92 |
| 23 | PLGA-COOH (1,650) | NaHCO$_3$ | PLGA-COONa | 1,650 | 98 |
| 24 | PLMA-COOH (1,096) | NaHCO$_3$ | PLMA-COONa | 1,096 | 96 |
| 25 | 3arm PLA-COOH (3,000) | NaHCO$_3$ | 3arm PLA-COONa | 3,000 | 98 |
| 26 | 5arm PLA-COOH (3,000) | NaHCO$_3$ | 5arm PLA-COONa | 3,000 | 98 |

PREPARATION EXAMPLE 27

Polymerization of a Monomethoxypolyethylene glycol-polylactide (mPEG-PLA) Block Copolymer (AB Type)

Five (5) grams of monomethoxypolyethylene glycol (Mn: 2,000 Daltons) were introduced into a 100 ml two-neck round-bottomed flask, and the mixture was dehydrated by heating to 100° C. under reduced pressure (1 mmHg) for 2 to 3 hours. The reaction flask was filled with dried nitrogen, and a reaction catalyst, stannous octoate (Sn(OCt)$_2$), was injected at 0.1 wt % (5 mg) of the lactide by using a syringe. The reaction mixture was stirred for 30 minutes, and the pressure was reduced to 1 mmHg at 110° C. for 1 hour to remove the solvent (toluene) dissolving the catalyst. Purified lactide (5 g) was added thereto, and the mixture was heated to 130° C. for 12 hours. The polymer formed was dissolved in ethanol, and diethyl ether was added thereto to precipitate the polymer. The polymer obtained was dried in a vacuum of the catalyst, stannous octoate, at 110° C. for 12 hours according to the same procedure as in Preparation Example 27. The mPEG-PLDO obtained had a number average molecular weight of 12,000-10,000 Daltons, and was confirmed to be of the AB type by $^1$H-NMR.

PREPARATION EXAMPLE 30

Polymerization of a Monomethoxypolyethylene glycol-polycaprolactone (mPEG-PCL) Block Copolymer (AB Type)

To synthesize an mPEG-PCL block copolymer, monomethoxypolyethylene glycol (Mn: 12,000 Daltons) was reacted with caprolactone in the presence of the catalyst, of stannous octoate, at 130° C. for 12 hours, according to the same procedure as in Preparation Example 27. The mPEG-PCL obtained had a number average molecular weight of 12,000-5,000 Daltons, and was confirmed be of the AB type by $^1$H-NMR.

The block copolymers synthesized from the above Preparation Examples 27 to 30 are shown in the following Table 4.

TABLE 4

| Preparation Example | Amphiphilic block copolymer | Mn (Daltons) | Yield (%) |
|---|---|---|---|
| 27 | mPEG-PLA | 2,000-1,765 | 86 |
| 28 | mPEG-PLGA | 5,000-4,000 | 90 |
| 29 | mPEG-PLDO | 12,000-10,000 | 78 |
| 30 | mPEG-PCL | 12,000-5,000 | 93 |

PREPARATION EXAMPLE 31

Polymerization of a Monomethoxypolyethylene glycol-monomethoxypolyethylene Glycol (PLA-mPEG-PLA) Block Copolymer (BAB Type)

PLA-mPEG-PLA was obtained according to the same procedure as in Preparation Example 27 except that 25 g of methoxypolyethylene glycol (MW=2,000) and 50 g of D,L-lactide were used. The PLA-mPEG-PLA obtained had a number average molecular weight of 1,765-2,000-1,765 Daltons, and was confirmed to be the BAB type by $^1$H-NMR.

EXAMPLE 1

Polymerization 1 of mPEG-PLA-cholesterol a) Synthesis of Cholesterol Succinate 7.6 grams of cholesterol and 2.36 grams of succinic anhydride were dissolved in 100 ml of 1,4-dioxane in a round-bottomed flask. A reaction catalyst, 2.9 grams of 4-(dimethylamino)pyridine (DMAP), was added thereto, and the mixture was stirred at room temperature for 24 hours. The reaction mixture was introduced into an HCl solution in order to precipitate the cholesterol succinate (9.1 g; yield=95%).

b) Binding of mPEG-PLA and Cholesterol Succinate

Figure 6:
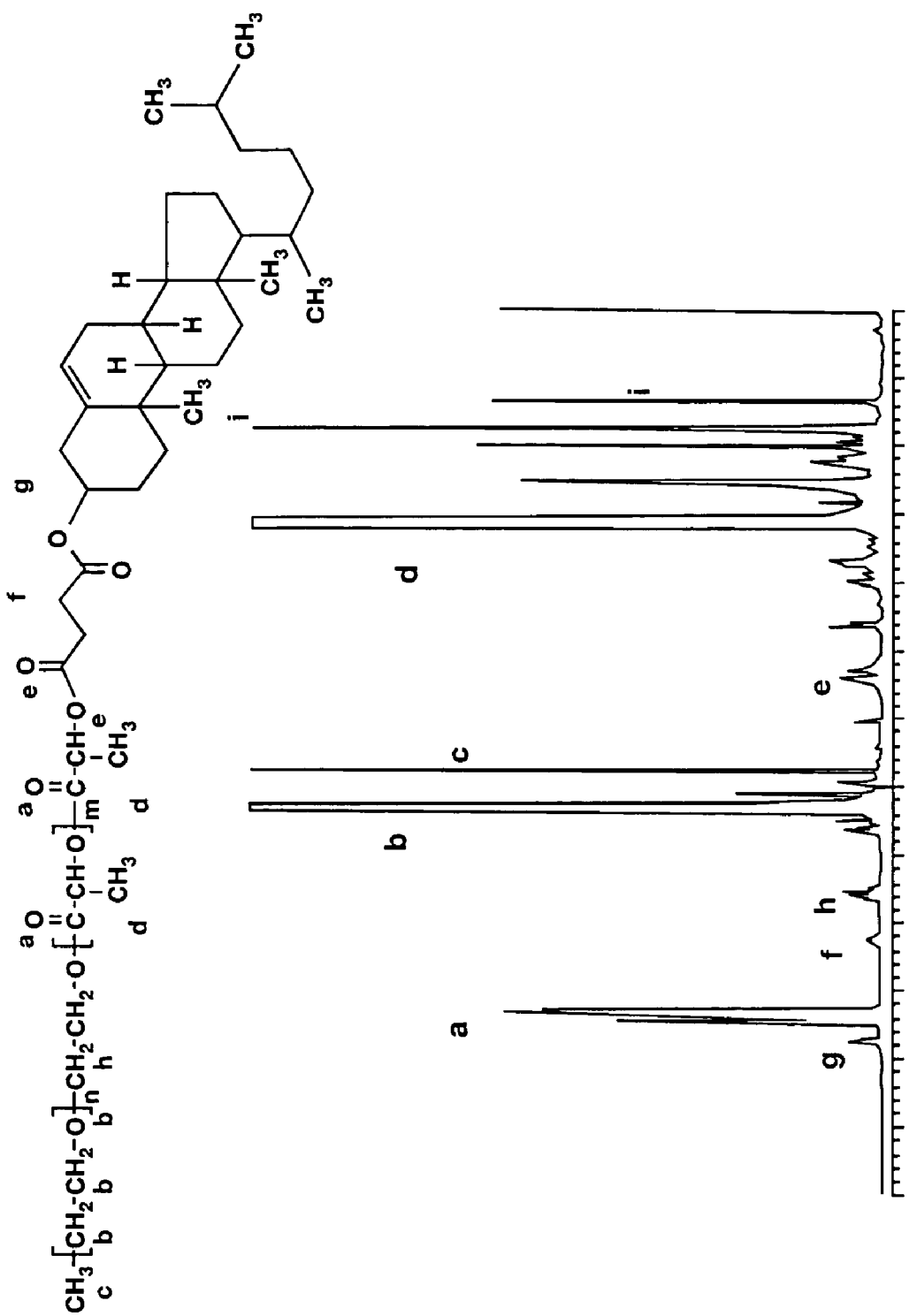
FIG. 6 is an $^1$H-NMR spectrum of mPEG-PLA-cholesterol (Example 1)

Ten (10) grams of mPEG-PLA synthesized from Preparation Example 27 and 1.55 grams (1.2-fold moles of the polymer) of cholesterol succinate were dissolved in 50 ml of acetonitrile in a round-bottomed flask. The reaction catalysts, 0.76 gram of dicyclohexylcarbodiimide (DCC) and 0.045 gram of 4-(dimethylamino)pyridine (DMAP), were added thereto, and the mixture was stirred at room temperature for 24 hours. Upon completion of the reaction, the mixture was filtered using a glass filter to remove dicyclohexylcarbourea, a byproduct. The residual catalyst was removed by extraction with a hydrochloric acid aqueous solution. To the purified product solution was added magnesium sulfate to remove any residual moisture, and the mixture was added into a cosolvent composed of n-hexane/diethyl ether (v/v=7/3) for recrystallization to occur in order to obtain a purified mPEG-PLA-cholesterol (10 g; yield=88.6%). Its NMR spectrum is as shown in FIG. 6.

EXAMPLE 2

Polymerization 2 of mPEG-PLA-cholesterol a) Synthesis of Cholesterol Succinate 7.6 grams of cholesterol and succinyl chloride (twice moles of cholesterol) were introduced into a flask, and dissolved in 50 ml of acetonitrile. The reaction to bind the succinate group to the hydroxyl group of cholesterol was performed at 50° C. for 12 hours, and was then precipitated in an HCl aqueous solution obtaining cholesterol succinate (8.2 g: yield 92%).

b) Binding of mPEG-PLA and Cholesterol Succinate mPEG-PLA-cholesterol (9.52 g: yield 85%) was obtained according to the same procedure as in Example 1b) except that 10 grams of mPEG-PLA and cholesterol succinate synthesized from Example 2a) (1.2-fold moles of the polymer) were used.

EXAMPLES 3 to 5

Polymerizations 3 to 5 of mPEG-PLA-cholesterol mPEG-PLA-cholesterol was obtained according the same procedure as in Example 2 except that malonyl chloride (Example 3), glutaryl chloride (Example 4), and adipoyl chloride (Example 5) each were used at twice the moles of the polymer.

EXAMPLES 6 to 9

Figure 7:
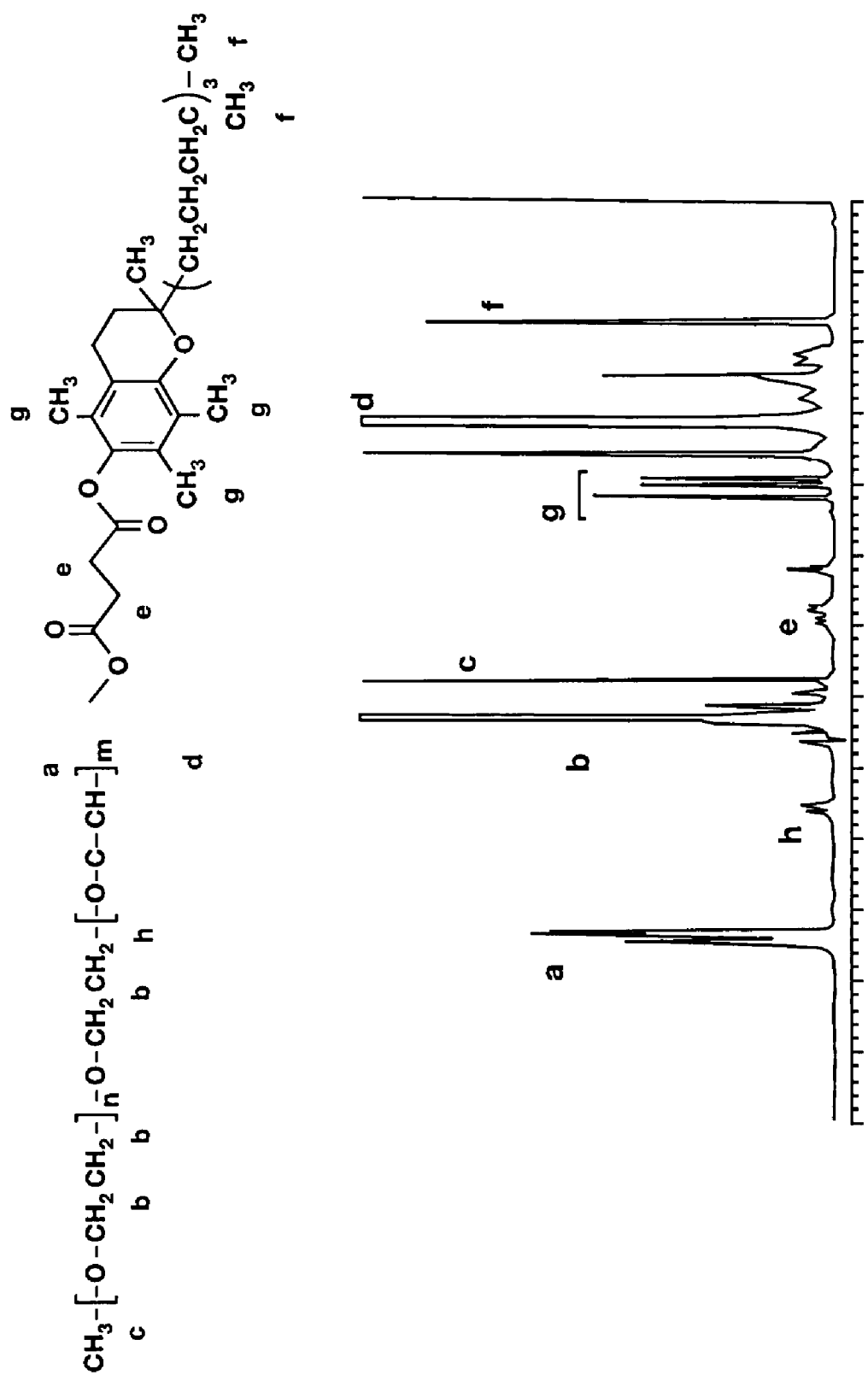
FIG. 7 is an $^1$H-NMR spectrum of mPEG-PLA-tocopherol (Example 7)

Polymerizations 1 to 4 of mPEG-PLA-tocopherol mPEG-PLA-tocopherol was obtained according the same procedure as in Example 2 except that 8.5 g of tocopherol, and malonyl chloride (Example 6), succinyl chloride (Example 7), glutaryl chloride (Example 8), and adipoyl chloride (Example 9) each were used at twice the moles of the polymer. Its NMR spectrum is as shown in FIG. 7 (for Example 7).

EXAMPLE 10

Polymerization of a Monomethoxypolyethylene glycol-poly(lactic-co-glycolide) Tocopherol (mPEG-PLGA-tocopherol) Block Copolymer (AB Type)

Purified mPEG-PLGA-tocopherol (10 g; yield=87.5%) was obtained according to the same procedure as in Example 1b) except a 10 g of mPEG-PLGA synthesized from Preparation Example 28 and 1.767 grams of tocopherol succinate was used.

EXAMPLE 11

Polymerization of a Monomethoxypolyethylene glycol-poly(lactic-co-glycolide) Cholesterol (mPEG-PLGA-cholesterol) Block Copolymer (AB Type)

Purified mPEG-PLGA-cholesterol (10 g; yield=88.6%) was obtained according to the same procedure as in Example 1b) except that 10 g of mPEG-PLGA synthesized from Preparation Example 28 and 0.70 g of cholesterol succinate was used.

EXAMPLE 12

Polymerization of a Monomethoxypolyethylene glycol-poly(lactic-co-p-dioxan-2-one) Tocopherol (mPEG-PLDO-tocopherol) Block Copolymer (AB Type)

Purified mPEG-PLDO-tocopherol (10 g; yield=87.5%) was obtained according to the same procedure as in Example 1b) except that 10 g of mPEG-PLDO synthesized from Preparation Example 29 and 0.314 g of tocopherol succinate were used.

EXAMPLE 13

Polymerization of a Monomethoxypolyethylene glycol-poly(lactic-co-dioxan-2-one) Cholesterol (mPEG-PLDO-cholesterol) Block Copolymer (AB Type)

Purified mPEG-PLDO-cholesterol (10 g; yield=88.6%) was obtained according to the same procedure as in Example 1b) except that 10 g of mPEG-PLDO synthesized from Preparation Example 29 and 0.288 g of cholesterol succinate were used.

EXAMPLE 14

Polymerization of a Monomethoxypolyethylene glycol-polycaprolactone tocopherol (mPEG-PCL-tocopherol) Block Copolymer (AB Type)

Purified mPEG-PCL-tocopherol (10 g; yield=87.5%) was obtained according to the same procedure as in Example 1b) except that 10 g of mPEG-PCL synthesized from Preparation Example 30 and 0.406 g of tocopherol succinate were used.

EXAMPLE 15

Polymerization of a Monomethoxypolyethylene glycol-polycaprolactone cholesterol (mPEG-PCL-cholesterol) Block Copolymer (AB Type)

Purified mPEG-PCL-cholesterol (10 g; yield=88.6%) was obtained according to the same procedure as in Example 1b) except that 10 g of mPEG-PCL synthesized from Preparation Example 30 and 0.372 grams of cholesterol succinate were used.

EXAMPLE 16

Polymerization 6 of mPEG-PLA-cholesterol

Four (4) grams of cholesterol was weighed, and dehydrated using a vacuum pump at 50° C. Thereto was added succinyl chloride (3.0 g; 2.0-fold moles of cholesterol) and the reaction was performed for 12 hours. After the reaction was completed, the excess added succinyl chloride was removed under vacuum at 100° C. Thereto was added mPEG-PLA (36 g; 0.95-fold mole of cholesterol), and the reaction was performed for 12 hours. The synthesized polymer was dissolved in methylene chloride, and then, precipitated in a hexane/diethyl ether solvent in order to obtain the amphiphilic block copolymer with the cholesterol group, mPEG-PLA-cholesterol. The precipitated polymeric product was filtered, and then dried under vacuum to obtain the polymer (35 g; yield 88%) as white particles.

EXAMPLES 17 to 20

Polymerizations 7 to 10 of mPEG-PLA-cholesterol mPEG-PLA-cholesterol was obtained according to the same procedure as in Example 16 except that oxalyl chloride (Example 17), malonyl chloride (Example 18), glutaryl chloride (Example 19), and adipoyl chloride (Example 20) were used at 2-fold moles of cholesterol, respectively.

EXAMPLES 21-25

Polymerizations 5 to 9 of mPEG-PLA-tocopherol mPEG-PLA-tocopherol was obtained according to the same procedure as in Example 16 except that 4.3 g of tocopherol was used, and oxalyl chloride (Example 21), malonyl chloride (Example 22), succinyl chloride (Example 23), glutaryl chloride (Example 24) and adipoyl chloride (Example 25) were used at 2-fold moles of tocopherol, respectively.

EXAMPLE 26

Polymerization 11 of mPEG-PLA-cholesterol

Cholesterol succinate (4.9 g) and oxalyl chloride (2.53 g; 2-fold moles of cholesterol succinate) were weighed, and reacted at 50° C. for 6 hours. After the reaction was completed, excess oxalyl chloride was removed under vacuum. mPEG-PLA (36 g; 0.95-fold moles of cholesterol succinate) was weighed and added thereto. The reaction temperature was set at 100° C., and the reaction was performed for 12 hours. The synthesized polymer was dissolved in methylene chloride, and then precipitated in hexane/diethyl ether, and filtered. The product was dried under vacuum to obtain mPEG-PLA-cholesterol (34.6 g; yield 91%).

EXAMPLES 27-29

Polymerizations 12-to 14 of mPEG-PLA-cholesterol mPEG-PLA-cholesterol was obtained according to the same procedure as in Example 26 except using cholesterol malonate (Example 27), cholesterol glutarate (Example 28) and cholesterol adipate (Example 29).

EXAMPLE 30-33

Polymerizations 10 to 13 of mPEG-PLA-tocopherol mPEG-PLA-tocopherol was obtained according to the same procedure as in Example 26 except that tocopherol malonate (Example 30), tocopherol succinate (Example 31), tocopherol glutarate (Example 32), and tocopherol adipate were used (Example 33).

EXAMPLE 34

Preparation of tocopherol-PLA-mPEG-PLA-tocopherol

Tocopherol-PLA-mPEG-PLA-tocopherol (yield=92.4%) was obtained according to the same procedure as in Example 1b) except that 10 g of PLA-mPEG-PLA synthesized from Preparation Example 31 and tocopherol succinate (2.4-fold moles of the polymer) were used.

EXAMPLE 35

Preparation of cholesterol-PLA-mPEG-PLA-cholesterol

Cholesterol-PLA-PEG-PLA-cholesterol (yield=94.2%) was obtained according to the same procedure as in Example 1b) except that 10 g of PLA-mPEG-PLA synthesized from Preparation Example 31 was used.

EXAMPLE 36

Pharmacokinetics for the Paclitaxel-Containing Polymeric Micelles of the Amphiphilic Diblock Copolymers Conjugated with the Hydrophobic Moiety To evaluate the effect of a hydrophobic moiety being substituted for the hydroxyl terminal group of the hydrophobic B block of the amphiphilic diblock copolymers (mPEG-PLA, Mn 2000-1765) on the bloodstream retention time of the paclitaxel-containing polymeric micelles, the compositions were prepared as follows. Paclitaxel and the amphiphilic diblock copolymer of Example 1, 7, or Preparation Example 27, were admixed in a weight ratio of 1:99, and then the mixture was dissolved in 5 ml of anhydrous ethanol to prepare a clear solution. Ethanol was removed therefrom using a vacuum evaporator to prepare a paclitaxel-containing polymeric composition. Distilled water (4 ml) was added thereto, and the mixture was stirred for 10 minutes at 60° C. to prepare a polymeric micelle aqueous solution containing paclitaxel. The mixture was passed through a filter with a pore size of 200 nm, and was then lyophilized.

The above composition and the drug content are summarized in Table 5.

TABLE 5

| | mPEG-PLA-tocopherol (mg) | Paclitaxel (mg) | Content of paclitaxel (mg/ml) |
|---|---|---|---|
| Comp. 1 | 990 | 10 | 1.5 |
| | mPEG-PLA-cholesterol (mg) | Paclitaxel (mg) | Content of paclitaxel (mg/ml) |
| Comp. 2 | 990 | 10 | 1.5 |
| | mPEG-PLA-COOH (mg) | Paclitaxel (mg) | Content of paclitaxel (mg/ml) |
| Comp. 3 | 990 | 10 | 1.5 |

For the animal experiments, male Sprague-Dawley rats weighing 250-300 g were cannulated in the vena femoralis and aorta femoralis. Compositions 1 to 3 were injected into the vena femoralis at a dose of 5 mg/kg over 15 seconds. After the injection, 0.3 ml of the whole blood was taken from the aorta femoralis at 1, 5, 15, and 30 minutes, and in 1, 2, 3, 4, and 6 hours, and then centrifuged to obtain clear supernatant plasma.

To analyze the plasma concentration of drug, 0.1 ml of the plasma was introduced into a covered glass tube, and 0.1 ml of an acetonitrile solution containing the internal standard substance was added thereto. Ten (10) ml of ethyl acetate was added to the above solution, and the mixture was vigorously stirred for 30 seconds, and then centrifuged at 2,500 rpm for 10 minutes. The whole ethyl acetate layer was taken and transferred to a test tube, and then the organic solvent was completely evaporated at 40° C. under nitrogen flow. Thereto was added 0.1 ml of a 40% (v/v) acetonitrile solution, and the mixture was vigorously stirred for 30 seconds, and then subjected to HPLC. The conditions for HPLC were as follows:

Injection Volume: 0.075 ml
Flow Rate: 1.0 ml/min
Wavelength: 227 nm
Mobile Phase: 24% aqueous acetonitrile solution for 5 minutes, increased to 58% for 16 minutes, increased to 70% for 2 minutes, decreased to 34% for 4 minutes, and maintained for 5 minutes
Column: 4.6×50 nm (C18, Vydac, USA).

The micelle size and analysis of the results of the plasma concentrations of the drugs are shown in the following Table 6 and FIG. 8.

TABLE 6

| | CMC (µg/ml) | Size (nm) | Plasma concentration of paclitaxel (µg/ml) | | | | | | | | |
|---|---|---|---|---|---|---|---|---|---|---|---|
| | | | 1 m | 5 m | 15 m | 30 m | 1 h | 2 h | 3 h | 4 h | 6 h |
| Comp. 1 | 10 | 30.9 | 111.5 | 31.6 | 15.7 | 8.68 | 4.21 | 1.72 | 1.03 | 0.72 | 0.43 |
| Comp. 2 | 18 | 50.6 | 98.2 | 28.9 | 13.6 | 6.84 | 2.82 | 1.26 | 0.65 | 0.43 | 0.26 |
| Comp. 3 | 20 | 27.1 | 51.0 | 9.76 | 4.63 | 2.25 | 0.91 | 0.28 | 0.19 | 0.14 | 0.05 |

Figure 8:
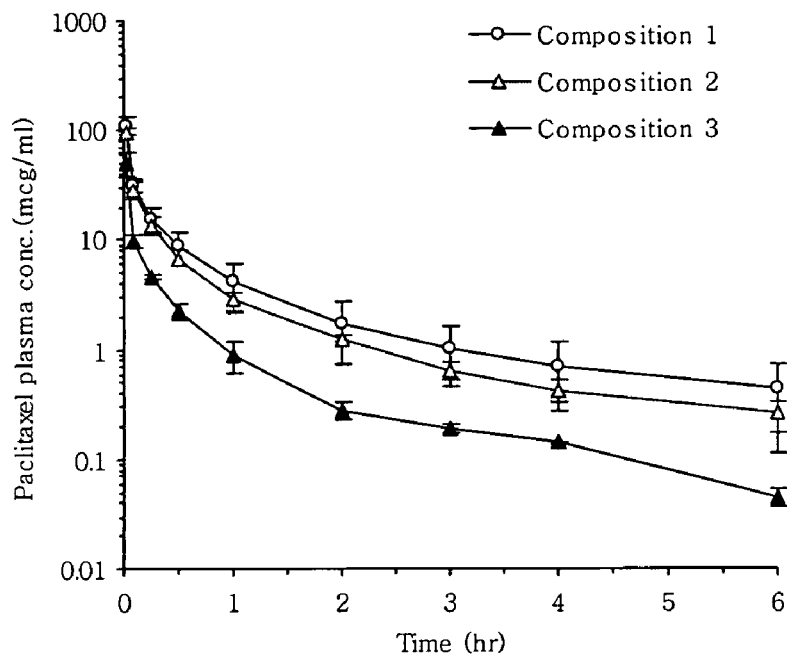
FIG. 8 shows the profile of plasma drug concentration of paclitaxel-containing polymeric micelles fabricated with various di-block copolymers at various time intervals after administration.

As shown in Table 6 and FIG. 8, the polymeric micelles (Compositions 1 and 2) of the amphiphilic diblock copolymers with a hydrophobic moiety (tocopherol succinic acid or cholesterol succinic acid) substituted on the hydroxyl terminal group of the hydrophobic B block had a much longer bloodstream retention time than the native mPEG-PLA-OH polymeric micelles (Composition 3). This result suggests that an increase of hydrophobicity of the hydrophobic B block in the amphiphilic polymer results in formation of more stable micelles due to stronger interactions between the hydrophobic moiety of the amphiphilic polymer and drug.

In addition, it was confirmed that the mPEG-PLA-tocopherol micelles (Composition 1) were circulated longer than the mPEG-PLA-cholesterol micelles (Composition 2) in the blood.

EXAMPLE 37

Preparation of Ionically Fixed Polymeric Micelles

Step 1: Preparation of the Polymeric Micelles of D,L-PLA-COONa and mPEG-PLA-tocopherol Block Copolymers 248.1 mg (0.218 mmol) of D,L-PLA-COONa (Mn: 1,140) from Preparation Example 15 and 744.3 mg of mPEG-PLA-tocopherol (Mn: 2,000-1,800 Daltons) from Example 7 were completely dissolved in 5 ml of ethanol to obtain a clear solution. Ethanol was removed therefrom to prepare a polymeric composition. Distilled water (6.2 ml) was added thereto and the mixture was stirred for 30 minutes at 60° C. to prepare the polymeric micelle aqueous solution.

Step 2: Fixation with the Di-Valent Metal Ion 0.121 ml (0.109 mmol) of a 0.9 M aqueous solution of anhydrous calcium chloride was added to the polymeric micelle aqueous solution prepared in Step 1, and the mixture was stirred for 20 minutes at room temperature. The mixture was passed through a filter having a pore size of 200 nm, and then was lyophilized. The particle size measured according to the Dynamic Light Scattering (DLS) Method was 25 nm.

EXAMPLE 38

Preparation of $Ca^{2+}$-Fixed Paclitaxel-Containing Micelles of D,L-PLA-COONa and mPEG-PLA-tocopherol Block Copolymers Step 1: Preparation of paclitaxel-containing polymeric micelles of D,L-PLA-COONa and mPEG-PLA-tocopherol Block Copolymers 248.1 mg (0.218 mmol) of D,L-PLA-COONa (Mn: 1,140) from Preparation Example 15, 7.5 mg of paclitaxel, and 744.3 mg of mPEG-PLA-tocopherol (Mn: 2,000-1,800 Daltons) from Example 7 were completely dissolved in 5 ml of ethanol to obtain a clear solution. Ethanol was removed therefrom to prepare a paclitaxel-containing polymeric composition. Distilled water (6.2 ml) was added thereto and the mixture was stirred for 30 minutes at 60° C. to prepare a paclitaxel-containing polymeric micelle aqueous solution.

Step 2: Fixation with the Divalent Metal Ion 0.121 ml (0.109 mmol) of a 0.9 M aqueous solution of anhydrous calcium chloride was added to the polymeric micelle aqueous solution prepared in Step 1, and the mixture was stirred for 20 minutes at room temperature. The mixture was passed through a filter having a pore size of 200 nm, and then was lyophilized. The content and solubility of paclitaxel were measured by HPLC and the particle size was measured according to the Dynamic Light Scattering (DLS) Method.

D,L-PLA-COONa/mPEG-PLA-tocopherol (weight ratio): 1/3

Content of Paclitaxel: 0.75 wt %

Particle Size: 29 nm

EXAMPLE 39

Preparation of $Mg^{2+}$-Fixed Paclitaxel-Containing Polymeric Micelles of D,L-PLMA-COONa and mPEG-PLA-tocopherol Block Copolymers A $Mg^{2+}$-fixed paclitaxel-containing polymeric micelle composition was prepared according to the same procedure as in Example 38 except that 248.1 mg (0.226 mmol) of D,L-PLMA-COONa (Mn: 1,096) from Preparation Example 24, 7.5 mg of paclitaxel and 744.3 mg of mPEG-PLA-tocopherol (Mn: 2,000-1,800 Daltons) from Example 7, and 0.230 ml (0.113 mmol) of the 0.5 M aqueous solution of magnesium chloride 6 hydrate (Mw: 203.31) were used.

D,L-PLMA-COONa/mPEG-PLA-tocopherol (weight ratio): 1/3

Content of Paclitaxel: 0.75 wt %

Particle Size: 30 nm

EXAMPLE 40

Preparation of $Ca^{2+}$-Fixed Paclitaxel-Containing Polymeric Micelles of D,L-PLMA-COONa and mPEG-PLA-tocopherol Block Copolymers A $Ca^{2+}$-fixed paclitaxel-containing polymeric micelle composition was prepared according to the same procedure as in Example 38 except that 248.1 mg (0.226 mmol) of D,L-PLMA-COONa (Mn: 1,096) from Preparation Example 24, 7.5 mg of paclitaxel and 744.4 mg of mPEG-PLA-tocopherol (Mn: 2,000-1,800 Daltons) from Example 7, and 0.126 ml (0.113 mmol) of the 0.9 M aqueous solution of anhydrous calcium chloride were used.

D,L-PLMA-COONa/mPEG-PLA-tocopherol (weight ratio): 1/3

Content of Paclitaxel: 0.75 wt %

Particle Size: 34 nm

EXAMPLE 41

Preparation of $Ca^{2+}$-Fixed Paclitaxel-Containing Polymeric Micelles of D,L-PLA-COOK and mPEG-PLA-cholesterol Block Copolymers A $Ca^{2+}$-fixed paclitaxel-containing polymeric micelle composition was prepared according to the same procedure as in Example 38 except that 248.1 mg (0.160 mmol) of D,L-PLA-COOK (Mn: 1,550) from Preparation Example 18, 7.5 mg of paclitaxel and 744.4 mg of mPEG-PLA-cholesterol (Mn: 2,000-1,800 Daltons) from Example 1, and 0.089 ml (0.080 mmol) of the 0.9 M aqueous solution of anhydrous calcium chloride were used.

D,L-PLMA-COONa/mPEG-PLA-cholesterol (weight ratio): 1/3

Content of Paclitaxel: 0.75 wt %

Particle Size: 34 nm

EXAMPLE 42

Preparation of $Ca^{2+}$-Fixed Paclitaxel-Containing Polymeric Micelles of D,L-PLMA-COONa and mPEG-PLA-cholesterol Block Copolymers A $Ca^{2+}$-fixed paclitaxel-containing polymeric micelle composition was prepared according to the same procedure as in Example 38 except that 248.1 mg (0.226 mmol) of D,L-PLMA-COONa (Mn: 1,096) from Preparation Example 24, 7.5 mg of paclitaxel and 744.4 mg of mPEG-PLA-cholesterol (Mn: 2,000-1,800 Daltons) from Example 1, and 0.126 ml (0.113 mmol) of the 0.9 M aqueous solution of anhydrous calcium chloride were used.

D,L-PLMA-COONa/mPEG-PLA-cholesterol (weight ratio): 1/3

Content of Paclitaxel: 0.75 wt %

Particle Size: 34 nm

EXAMPLE 43

Preparation of $Ca^{2+}$-Fixed Paclitaxel-Containing Polymeric Micelles of 3 arm PLA-COONa and mPEG-PLA-tocopherol Block Copolymers A $Ca^{2+}$-fixed paclitaxel-containing polymeric micelle composition was prepared according to the same procedure as in Example 38 except that 248.1 mg (0.0827 mmol) of 3 arm PLA-COONa (Mn: 3,000) from Preparation Example 25, 7.5 mg of paclitaxel and 744.4 mg of mPEG-PLA-tocopherol (Mn: 2,000-1,800 Daltons) from Example 7, and 0.1377 ml (0.124 mmol)of the 0.9 M aqueous solution of anhydrous calcium chloride were used.

3arm PLACOONa/mPEG-PLA-tocopherol (weight ratio): 1/3
Content of Paclitaxel: 0.75 wt %
Particle Size: 29 nm

EXAMPLE 44

Preparation of $Ca^{2+}$-Fixed Paclitaxel-Containing Polymeric Micelles of 5 arm PLA-COONA and mPEG-PLA-tocopherol Block Copolymers A $Ca^{2+}$-fixed paclitaxel-containing polymeric micelle composition was prepared according to the same procedure as in Example 38 except that 248.1 mg (0.0827 mmol) of 5 arm PLA-COONa (Mn: 3,000) from Preparation Example 26, 7.5 mg of paclitaxel and 744.4 mg of mPEG-PLA-tocopherol (Mn: 2,000-1,800 Daltons) from Example 7, and 0.2295 ml (0.207 mmol) of the 0.9 M aqueous solution of anhydrous calcium chloride were used.

5arm PLACOONa/mPEG-PLA-tocopherol (weight ratio): 1/3
Content of Paclitaxel: 0.75 wt %
Particle Size: 29 nm

EXAMPLE 45

Preparation of Doxorubicin-Containing Polymeric Micelles of D,L-PLMA-COONa and mPEG-PLA-tocopherol Block Copolymers mPEG-PLA-tocopherol (Mn: 2,000-1,800), D,L-PLMA-COONa (Mn: 969), and doxorubicin HCl were admixed in a weight ratio of 78.62:17.24:1.00, and then the mixture was dissolved in 5 ml of anhydrous methanol to prepare a clear solution. Methanol was removed therefrom using a vacuum evaporator to prepare a doxorubicin-containing polymeric composition. Distilled water (4 ml) was added thereto, and the mixture was stirred for 10 minutes at 60° C. to prepare a polymeric micelle aqueous solution containing doxorubicin. The mixture was passed through a filter with a pore size of 200 nm, and then was lyophilized.

D,L-PLMA-COONa/mPEG-PLA-tocopherol (weight ratio): 1/4.56
Content of doxorubicin: 1.03 wt %
Particle Size: 35 nm

EXAMPLE 46

Preparation of Epirubicin-Containing Polymeric Micelles of D,L-PLMA-COONa and mPEG-PLA-tocopherol Block Copolymers mPEG-PLA-tocopherol (Mn: 2,000-1,800), D,L-PLMA-COONa (Mn: 969), and epirubicin HCl were admixed in a weight ratio of 78.62:17.24:1.00, and then the mixture was dissolved in 5 ml of anhydrous methanol to prepare a clear solution. Methanol was removed therefrom using a vacuum evaporator to prepare an epirubicin-containing polymeric composition. Distilled water (4 ml) was added thereto and the mixture was stirred for 10 minutes at 60° C. to prepare a polymeric micelle aqueous solution containing doxorubicin. The mixture was passed through a filter with a pore size of 200 nm, and than was lyophilized.

D,L-PLMA-COONa/mPEG-PLA-tocopherol (weight ratio): 1/4.56
Content of epirubicin: 1.03 wt %
Particle Size: 30 nm

EXAMPLE 47

Particle Size for the $Ca^{2+}$-Fixed Polymeric Micelles

To determine the particle size of the $Ca^{2+}$-fixed polymeric micelles, the polymeric micelle compositions were prepared as follows.

mPEG-PLA (Mn: 2,000-1,800) and D,L-PLMA-COONa (Mn: 866, 994, 1,156, 1,536) were admixed in an equivalent ratio of 1:1, and then the mixture was dissolved in 5 ml of anhydrous ethanol to prepare a clear solution. Ethanol was removed therefrom using a vacuum evaporator to prepare a polymeric composition. Distilled water was added thereto and the mixture was stirred for 10 minutes at 60° C. to prepare a polymeric micelle aqueous solution containing paclitaxel. To the above polymeric micelle solution was added a $CaCl_2$ aqueous solution (concentration: 100 mg/ml) of the same number equivalents as the D,L-PLMA-COONa solution, and the mixture was stirred for 20 minutes at room temperature. The mixture was passed through a filter with a pore size of 200 nm, and then PBS buffer at a pH of 7.4 was added thereto to dilute the mixture to make a 40 mg/ml concentration of the polymers. The particle size was measured with a photon correlation particle size analyzer after filtration using a 0.22 um membrane filter.

TABLE 7

| | | | | Particle size (nm) | |
| --- | --- | --- | --- | --- | --- |
| Mn of D,L-PLMA-COONa | mPEG-PLA-Tocopherol (mg) | D,L-PLMA-COONa (mg) | $CaCl_2$ (mg) | Before the treatment of $Ca^{2+}$ | After the treatment of $Ca^{2+}$ |
| 866 | 380.0 | 86.6 | 5.55 | 20.5 | 27.9 |
| 994 | 380.0 | 99.4 | 5.55 | 15.4 | 29.6 |
| 1156 | 380.0 | 115.6 | 5.55 | 21.2 | 32.7 |
| 1536 | 380.0 | 153.6 | 5.55 | 25.7 | 35.8 |

As shown in Table 7, the particle size of the $Ca^{2+}$-fixed polymeric micelles had an average size of 20-40 nm. Micelles of this size range are suitable for injection formulations and sterile filtration. As the molecular weight of the D,L-PLMA-COONa increased from 866 to 1536, the particle size increased slightly in both the $Ca^{2+}$ treated and non-treated micelles. The particle size of the $Ca^{2+}$-fixed polymeric micelles was larger by approximately 10 nm than the micelles not treated with $Ca^{2+}$.

EXAMPLE 48

Kinetic Stability for the $Ca^{2+}$-Fixed Paclitaxel-Containing Polymeric Micelles To test the stability of the nanoparticle composition, the polymeric micelle compositions were prepared as follows.

(Composition 4) Paclitaxel, mPEG-PLA-Tocopherol (Mn: 2,000-1,800), and D,L-PLMA-COONa (Mn: 1,096) were admixed at an equivalent ratio of 1:3:3, and then the mixture was dissolved in 5 ml of anhydrous ethanol to prepare a clear solution. Ethanol was removed therefrom using a vacuum evaporator to prepare a paclitaxel-containing polymeric composition. Distilled water (4 ml) was added thereto, and the mixture was stirred for 10 minutes at 60° C. to prepare a polymeric micelle aqueous solution containing paclitaxel. To the above polymeric micelle solution was added a $CaCl_2$ aqueous solution (concentration: 100 mg/ml) of the same number of equivalents as the D,L-PLMA-COONa, and the mixture was stirred for 20 minutes at room temperature. The mixture was passed through a filter with a pore size of 200 nm, and then was lyophilized. (Composition 5) Paclitaxel, mPEG-PLA-Tocopherol (Mn: 2,000-1,800) and D,L-PLMA-COONa (Mn: 1,096) were admixed at an equivalent ratio of 1:3:3 and then the mixture was dissolved in 5 ml of anhydrous ethanol to prepare a clear solution. Ethanol was removed therefrom using a vacuum evaporator to prepare a paclitaxel-containing polymeric composition. Distilled water (4 ml) was added thereto and the mixture was stirred for 10 minutes at 60° C. to prepare a polymeric micelle aqueous solution containing paclitaxel. The mixture was passed through a filter with a pore size of 200 nm, and then was lyophilized.

(Composition 6) Paclitaxel and mPEG-PLA-Tocopherol (Mn: 2,000-1,800) were admixed at an equivalent ratio of 1:3, and then the mixture was dissolved in 5 ml of anhydrous ethanol to prepare a clear solution. Ethanol was removed therefrom using a vacuum evaporator to prepare a paclitaxel-containing polymeric composition. Distilled water (5 ml) was added thereto, and the mixture was stirred for 10 minutes at 60° C. to prepare a polymeric micelle aqueous solution containing paclitaxel. The mixture was passed through a filter with a pore size of 200 nm, and then was lyophilized.

(Composition 7) Paclitaxel, mPEG-PLA (Mn: 2,000-1,765), and D,L-PLMA-COONa (Mn: 1,096) were admixed at an equivalent ratio of 1:3:3, and then the mixture was dissolved in 5 ml of anhydrous ethanol to prepare a clear solution. Ethanol was removed therefrom using a vacuum evaporator to prepare a paclitaxel-containing polymeric composition. Distilled water (4 ml) was added thereto, and the mixture was stirred for 10 minutes at 60° C. to prepare a polymeric micelle aqueous solution containing paclitaxel. To the above polymeric micelle solution was added a $CaCl_2$ aqueous solution (concentration: 100 mg/ml) of the same number of equivalents as the D,L-PLMA-COONa, and the mixture was stirred for 20 minutes at room temperature. The mixture was passed through a filter with a pore size of 200 nm, and then was lyophilized.

TABLE 8

| | mPEG-PLA-Tocopherol (mg) | mPEG-PLA (mg) | D,L-PLMA-COONa (mg) | Paclitaxel (mg) | $CaCl_2$ (mg) | Content of paclitaxel (mg/ml) |
|---|---|---|---|---|---|---|
| Comp. 4 | 267.0 | — | 77.0 | 20.0 | 3.9 | 1.0 |
| Comp. 5 | 267.0 | — | 77.0 | 20.0 | — | 1.0 |
| Comp. 6 | 267.0 | — | — | 20.0 | — | 1.0 |
| Comp. 7 | — | 267.0 | 77.0 | 20.0 | 3.9 | 1.0 |

PBS buffer of a pH of 7.4 was added to the lyophilized compositions to make a 1.0 mg/ml concentration of paclitaxel. The mixture was allowed to stand at 37° C. and the concentration of paclitaxel over the lapse of time was measured by HPLC. The results are shown in Table 9.

TABLE 9

| | Drug concentration (mg/ml) | | | | | | | | |
|---|---|---|---|---|---|---|---|---|---|
| | 0 d | 1 d | 2 d | 3 d | 5 d | 7 d | 10 d | 12 d | 14 d |
| Comp. 4 | 1.00 | 0.97 | 0.94 | 0.93 | 0.81 | 0.72 | 0.60 | 0.54 | 0.45 |
| Comp. 5 | 1.00 | 0.93 | 0.84 | 0.78 | 0.61 | 0.48 | 0.41 | 0.36 | 0.30 |
| Comp. 6 | 1.00 | 0.80 | 0.48 | 0.41 | 0.34 | 0.26 | 0.21 | 0.20 | 0.19 |
| Comp. 7 | 1.00 | 0.85 | 0.63 | 0.59 | 0.57 | 0.49 | 0.44 | 0.40 | 0.37 |

As shown in Table 9, the $Ca^{2+}$-fixed paclitaxel-containing polymeric micelle composition (Composition 4) was kinetically more stable than the $Ca^{2+}$-nontreated composition (Composition 5). The addition of $Ca^{2+}$ significantly increased retention of the paclitaxel in the polymeric micelles of the present invention. This is due to the crosslinking electrostatic interaction of D,L-PLA-COO⁻ and $Ca^{2+}$ which might induce an increase in the rigidity of the hydrophobic core. The $Ca^{2+}$-fixed polymeric micelles (Composition 4) of the amphiphilic diblock copolymers with a hydrophobic moiety (tocopherol succinic acid) substituted for the hydroxyl terminal group of the hydrophobic B block had a much longer retention time than the $Ca^{2+}$-fixed polymeric micelles (Composition 7) of native mPEG-PLA-OH. This result also suggests that the increase of hydrophobicity of the hydrophobic B block in the amphiphilic polymer results in formation of more stable micelles due to stronger interactions between the hydrophobic moiety of the amphiphilic block copolymer and drug.

EXAMPLE 49

Pharmacokinetics for $Ca^{2+}$-Fixed Paclitaxel-Containing Polymeric Micelles To evaluate the effect of a hydrophobic moiety substituted for the hydroxyl terminal group of the hydrophobic B block of the amphiphilic di-block copolymers (mPEG-PLA, Mn 2000-1765) on the bloodstream retention time of the $Ca^{2+}$-fixed paclitaxel-containing polymeric micelles, the compositions were prepared as follows.

Paclitaxel, mPEG-PLA-tocopherol (Mn: 2,000-1,800) or mPEG-PLA-OH, and D,L-PLMA-COONa (Mn: 1,004) were admixed in a weight ratio of 74.25:24.75:1.00, and then the mixture was dissolved in 5 ml of anhydrous ethanol to prepare a clear solution. Ethanol was removed therefrom using a vacuum evaporator to prepare a paclitaxel-containing polymeric composition. Distilled water (4 ml) was added thereto, and the mixture was stirred for 10 minutes at 60° C. to prepare a polymeric micelle aqueous solution containing paclitaxel. To the above polymeric micelle solution was added a $CaCl_2$ aqueous solution (concentration: 100 mg/ml) of the same number of equivalents as the D,L-PLMA-COONa, and the mixture was stirred for 20 minutes at room temperature. The mixture was passed through a filter with a pore size of 200 nm, and then was lyophilized.

The above composition and the drug contents are summarized in Table 10.

TABLE 10

| | mPEG-PLA-Tocopherol (mg) | D,L-PLMA-COONa (mg) | Paclitaxel (mg) | $CaCl_2$ (mg) | Content of paclitaxel (mg/ml) |
|---|---|---|---|---|---|
| Comp. 8 | 742.5 | 247.5 | 10.0 | 13.7 | 1.5 |

| | mPEG-PLA (mg) | D,L-PLMA-COONa (mg) | Paclitaxel (mg) | $CaCl_2$ (mg) | Content of paclitaxel (mg/ml) |
|---|---|---|---|---|---|
| Comp. 9 | 742.5 | 247.5 | 10.0 | 13.7 | 1.5 |

For the animal experiments, male Sprague-Dawley rats weighing 220-270 g were cannulated in the vena femoralis and aorta femoralis. Compositions 8 and 9 were injected into the vena femoralis at a dose of 5 mg/kg over 15 seconds. After the injection, 0.3 ml of whole blood was taken from the aorta femoralis in 1, 5, 15, and 30 minutes, and in 1, 2, 3, 4, and 6 hours, and then centrifuged to obtain clear supernatant plasma.

The plasma drug concentration was analyzed according to the same process as in Example 36, and analysis of the results on the plasma concentrations of the drugs are shown in the following Table 11 and FIG. 9.

TABLE 11

| | Plasma concentration of paclitaxel (μg/ml) | | | | | | | | |
|---|---|---|---|---|---|---|---|---|---|
| | 1 m | 5 m | 15 m | 30 m | 1 h | 2 h | 3 h | 4 h | 6 h |
| Comp. 8 | 84.5 | 19.3 | 9.76 | 5.01 | 2.73 | 1.37 | 0.76 | 0.57 | 0.33 |
| Comp. 9 | 56.7 | 16.4 | 8.33 | 4.35 | 1.82 | 0.82 | 0.43 | 0.26 | 0.15 |

As shown in Table 11 and FIG. 9, the $Ca^{2+}$-fixed polymeric micelles (Composition 8) of the amphiphilic di-block copolymers with a hydrophobic moiety (tocopherol succinic acid) substituted for the hydroxyl terminal group of the hydrophobic B block had a much longer bloodstream retention time than the $Ca^{2+}$-fixed polymeric micelles (Composition 9) of native mPEG-PLA-OH. This result suggests, as demonstrated in Example 36, that the increase of hydrophobicity of the hydrophobic B block in the amphiphilic polymer results in formation of more stable micelles due to stronger interactions between the hydrophobic moiety of the amphiphilic polymer and drug.

EXAMPLE 50

Pharmacokinetics for the $Ca^{2+}$-Fixed Paclitaxel-Containing Polymeric Micelles To compare the bloodstream retention time of the $Ca^{2+}$-fixed paclitaxel-containing polymeric micelles with that of the formulations containing other carriers, the compositions were prepared as follows.

(Composition 10) $Ca^{2+}$-Fixed Paclitaxel-Containing Polymeric Micelles

Paclitaxel, mPEG-PLA-tocopherol (Mn: 2,000-1,800), and D,L-PLMA-COONa (Mn: 1,004) were admixed in a weight ratio of 99.25:33.08:1.00, and then the mixture was dissolved in 5 ml of anhydrous ethanol to prepare a clear solution. Ethanol was removed therefrom using a vacuum evaporator to prepare a paclitaxel-containing polymeric composition. Distilled water (4 ml) was added thereto, and the mixture was stirred for 10 minutes at 60° C. to prepare a polymeric micelle aqueous solution containing paclitaxel. To the above polymeric micelle solution was added a $CaCl_2$ aqueous solution (concentration: 100 mg/ml) of the same number of equivalents as the D,L-PLMA-COONa, and the mixture was stirred for 20 minutes at room temperature. The mixture was passed through a filter with a pore size of 200 nm, and then was lyophilized. The hydrodynamic particle size of the polymeric micelles was 34 nm.

(Composition 11) Composition Containing Paclitaxel, Cremophor EL, and Anhydrous Ethanol Paclitaxel (30 mg) was dissolved in 5 ml of a mixed solution (50:50 v/v) of Cremophor EL and anhydrous ethanol to obtain a clear solution. The solution was passed through a filter having a pore size of 200 nm.

(Composition 12) Composition Containing Paclitaxel, Polysorbate 80 (Tween 80), and Anhydrous Ethanol Paclitaxel (30 mg) was dissolved in 5 ml of a mixed solution (50:50 v/v) of polysorbate 80 and anhydrous ethanol to obtain a clear solution. The solution was passed through a filter having a pore size of 200 nm.

The above composition and the drug contents are summarized in Table 12.

TABLE 12

| | mPEG-PLA-Tocopherol (mg) | D,L-PLMA-COONa (mg) | Paclitaxel (mg) | $CaCl_2$ (mg) | Content of paclitaxel (mg/ml) |
|---|---|---|---|---|---|
| Comp. 10 | 1985.0 | 661.6 | 20.0 | 36.6 | 1.5 |

| | Cremophor EL (ml) | Anhydrous ethanol (ml) | Paclitaxel (mg) | | Content of paclitaxel (mg/ml) |
|---|---|---|---|---|---|
| Comp. 11 | 2.5 | 2.5 | 30.0 | — | 1.5 |

| | Tween 80 (ml) | Anhydrous ethanol (ml) | Paclitaxel (mg) | | Content of paclitaxel (mg/ml) |
|---|---|---|---|---|---|
| Comp. 12 | 2.5 | 2.5 | 30.0 | — | 1.5 |

For the animal experiments, male Sprague-Dawley rats weighting 230-250 g were cannulated in the vena femoralis and aorta femoralis. Compositions 10, 11 and 12 were injected into the vena femoralis at a dose of 5 mg/kg over 15 seconds. After the injection, 0.3 ml of the whole blood was taken from the aorta femoralis in 1, 5, 15, and 30 minutes, and in 1, 2, 3, 4, and 6 hours, and then centrifuged to obtain clear supernatant plasma.

The plasma drug concentration was analyzed according to the same process as in Example 36, and analysis of the results of the plasma concentrations of the drugs are shown in the following Table 13 and FIG. 10.

TABLE 13

| | Plasma concentration of paclitaxel (μg/ml) | | | | | | | | |
|---|---|---|---|---|---|---|---|---|---|
| | 1 m | 5 m | 15 m | 30 m | 1 h | 2 h | 3 h | 4 h | 6 h |
| Comp. 10 | 95.4 | 32.9 | 12.5 | 5.86 | 2.79 | 1.25 | 0.74 | 0.54 | 0.24 |
| Comp. 11 | 49.8 | 13.9 | 3.93 | 2.06 | 0.78 | 0.26 | 0.16 | 0.11 | 0.06 |
| Comp. 12 | 13.9 | 0.64 | 0.26 | 0.10 | 0.07 | 0.04 | — | — | — |

As shown in Table 13 and FIG. 10, the $Ca^{2+}$-fixed polymeric micelles (Composition 10) had a longer bloodstream retention time than the injections containing other surfactants (Compositions 11 and 12). Since the $Ca^{2+}$-fixed polymeric micelles (Composition 10) of the present invention had a longer bloodstream retention time than the marketed formulation, Taxol® (Composition 11), the present invention could increase the drug retention time in the bloodstream over Taxol® by using the biodegradable and biocompatible polymers of the present invention.

EXAMPLE 51

Pharmacokinetics for the $Ca^{2+}$-Fixed Paclitaxel-Containing Polymeric Micelles To compare the bloodstream retention time of the $Ca^{2+}$-fixed paclitaxel-containing polymeric micelles with that of the formulations containing other carriers, the compositions were prepared as follows.

(Composition 13) $Ca^{2+}$-Fixed Paclitaxel-Containing Polymeric Micelles

Paclitaxel, mPEG-PLA-tocopherol (Mn: 2,000-1,800), and 5arm PLA-COONa (Mn: 3,000) were admixed in a weight ratio of 99.25/33.08:1.00, and then the mixture was dissolved in 5 ml of anhydrous ethanol to prepare a clear solution. Ethanol was removed therefrom using a vacuum evaporator to prepare a paclitaxel-containing polymeric composition. Distilled water (4 ml) was added thereto, and the mixture was stirred for 10 minutes at 60° C. to prepare a polymeric micelle aqueous solution containing paclitaxel. To the above polymeric micelle solution was added a $CaCl_2$ aqueous solution (concentration: 100 mg/ml) of the same number of equivalents as the 5arm PLA-COONa, and the mixture was stirred for 20 minutes at room temperature. The mixture was passed through a filter with a pore size of 200 nm, and then was lyophilized. The hydrodynamic particle size of the polymeric micelles was 32 nm.

(Composition 11) Composition Containing Paclitaxel, Cremophor EL, and Anhydrous Ethanol Paclitaxel (30 mg) was dissolved in 5 ml of a mixed solution (50:50 v/v) of Cremophor EL and anhydrous ethanol to obtain a clear solution. The solution was passed through a filter having a pore size of 200 nm.

The above composition and the drug contents are summarized in Table 14.

TABLE 14

| | mPEG-PLA-Tocopherol (mg) | 5arm PLA-COONa (mg) | Paclitaxel (mg) | $CaCl_2$ (mg) | Content of paclitaxel (mg/ml) |
|---|---|---|---|---|---|
| Comp. 13 | 1985.0 | 661.6 | 20.0 | 11.7 | 1.0 |

| | Cremophor EL (ml) | Anhydrous ethanol (ml) | Paclitaxel (mg) | | Content of paclitaxel (mg/ml) |
|---|---|---|---|---|---|
| Comp. 11 | 2.5 | 2.5 | 30.0 | — | 1.0 |

For the animal experiments, male Sprague-Dawley rats weighing 230-250 g were cannulated in the vena femoralis and aorta femoralis. Compositions 13 and 11 were injected into the vena femoralis at a dose of 5 mg/kg over 15 seconds. After the injection, 0.3 ml of the whole blood was taken from the aorta femoralis in 1, 5, 15, and 30 minutes, and in 1, 2, 3, 4, and 6 hours, and then centrifuged to obtain clear supernatant plasma.

The plasma drug concentration was analyzed according to the same process as in Example 36, and analysis of the results of the plasma concentrations of the drugs are shown in the following Table 15 and FIG. 11.

TABLE 15

| | Plasma concentration of paclitaxel (μg/ml) | | | | | | | | |
|---|---|---|---|---|---|---|---|---|---|
| | 1 m | 5 m | 15 m | 30 m | 1 h | 2 h | 3 h | 4 h | 6 h |
| Comp. 13 | 53.6 | 16.9 | 7.14 | 3.21 | 1.40 | 0.63 | 0.40 | 0.28 | 0.14 |
| Comp. 11 | 45.9 | 10.8 | 4.56 | 2.15 | 0.75 | 0.33 | 0.18 | 0.11 | 0.08 |

Figure 11:
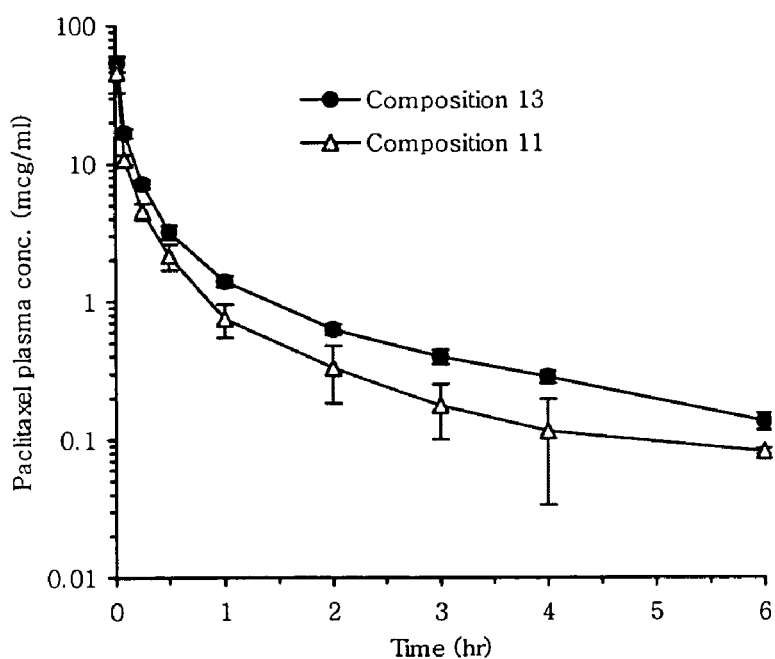
FIG. 11 shows the plasma drug concentration of paclitaxel-containing $Ca^{2+}$-fixed polymeric micelles and Cremophor EL (Taxol®) at various time intervals after administration.

As shown in Table 15 and FIG. 11, the $Ca^{2+}$-fixed polymeric micelles (Composition 13) had a longer bloodstream retention time than the injections containing other surfactants (Composition 11). Since the $Ca^{2+}$-fixed polymeric micelles (Composition 13) of the present invention had a longer bloodstream retention time than the marketed formulation, Taxol® (Composition 11), the present invention could increase the drug retention time in the bloodstream over Taxol® by using the biodegradable and biocompatible polymers of the present invention.

EXAMPLE 52

Pharmacokinetics for the $Ca^{2+}$-Fixed Docetaxel-Containing Polymeric Micelles To compare the bloodstream retention time of the $Ca^{2+}$-fixed docetaxel-containing polymeric micelles with that of the formulations containing other carriers, the compositions were prepared as follows.

(Composition 14) $Ca^{2+}$-Fixed Docetaxel-Containing Polymeric Micelles

Docetaxel, mPEG-PLA-Tocopherol (Mn: 2,000-1,800), and 3 arm PLA-COONa (Mn: 3,000) were admixed in a weight ratio of 99.25/33.08:1.00, and then the mixture was dissolved in 5 ml of anhydrous ethanol to prepare a clear solution. Ethanol was removed therefrom using a vacuum evaporator to prepare a docetaxel-containing polymeric composition. Distilled water (4 ml) was added thereto, and the mixture was stirred for 10 minutes at 60° C. to prepare a polymeric micelle aqueous solution containing docetaxel. To the above polymeric micelle solution was added a CaCl$_2$ aqueous solution (concentration: 100 mg/ml) of the same number of equivalents as the 3 arm-PLA-COONa, and the mixture was stirred for 20 minutes at room temperature. The mixture was passed through a filter with the pore size of 200 nm, and then was lyophilized. The hydrodynamic particle size of the polymeric micelles was 30 nm.

(Composition 15) Composition Containing Docetaxel, Polysorbate 80 (Tween 80), and Anhydrous Ethanol Docetaxel (20 mg) and Tween 80 (520 mg) were dissolved in 1.5 ml of 13% (v/v) ethanol aqueous solution to obtain a clear solution. The solution was passed through a filter having a pore size of 200 nm.

The above composition and the drug contents are summarized in Table 16.

TABLE 16

|  | mPEG-PLA-Tocopherol (mg) | 3 arm PLA-COONa (mg) | Docetaxel (mg) | CaCl$_2$ (mg) | Content of docetaxel (mg/ml) |
| --- | --- | --- | --- | --- | --- |
| Comp. 14 | 1985.0 | 661.6 | 20.0 | 36.6 | 1.0 |

|  | Tween 80 (ml) | 13% aqueous ethanol (ml) | Docetaxel (mg) |  | Content of docetaxel (mg/ml) |
| --- | --- | --- | --- | --- | --- |
| Comp. 15 | 520 | 1.5 | 20.0 | — | 1.0 |

For the animal experiments, male Sprague-Dawley rats weighing 210-240 g were cannulated in the vena femoralis and aorta femoralis. Compositions 14 and 15 were injected into the vena femoralis at a dose of 10 mg/kg over 15 seconds. After the injection, 0.3 ml of the whole blood was taken from the aorta femoralis in 5, 15, and 30 minutes, and in 1, 2, 3, 6, and 8 hours, and then centrifuged to obtain clear supernatant plasma.

Figure 12:
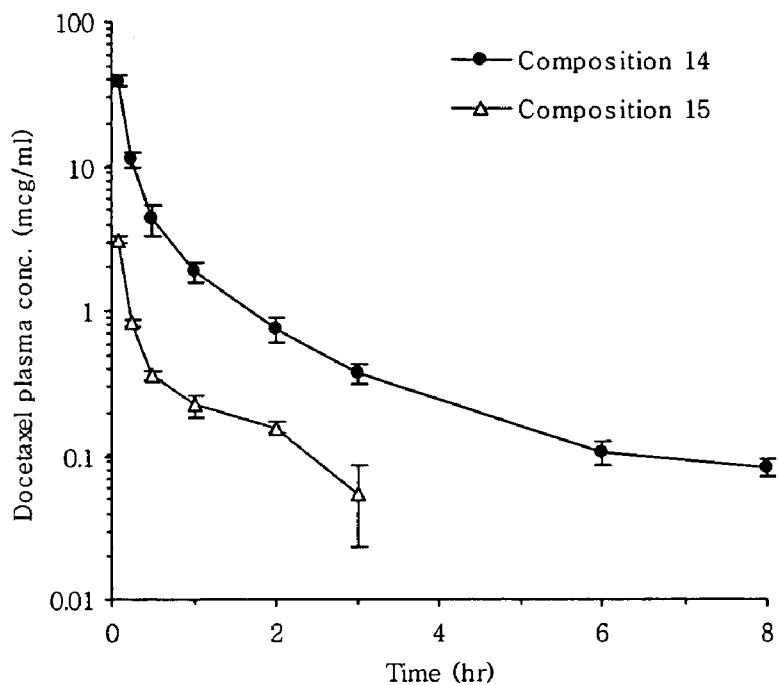
FIG. 12 shows the plasma drug concentration of docetaxel-containing $Ca^{2+}$-fixed polymeric micelles and Tween 80 preparations (Taxotere®) at various time intervals after administration.

The plasma drug concentration was analyzed according to the same process as in Example 36, and the results of the plasma drug concentrations are shown in Table 17 and FIG. 12.

TABLE 17

| | Plasma concentration of docetaxel (μg/ml) | | | | | | | |
| --- | --- | --- | --- | --- | --- | --- | --- | --- |
| | 5 m | 15 m | 30 m | 1 h | 2 h | 3 h | 6 h | 8 h |
| Com. 14 | 38.3 | 11.0 | 4.3 | 1.8 | 0.7 | 0.4 | 0.1 | 0.08 |
| Com. 15 | 3.1 | 0.83 | 0.36 | 0.23 | 0.16 | 0.05 | — | — |

As shown in Table 17 and FIG. 12, the Ca$^{2+}$-fixed polymeric micelles (Composition 14) had a longer bloodstream retention time than the injections containing Tween 80 (Composition 15). Since the Ca$^{2+}$-fixed polymeric micelles (Composition 14) of the present invention had a longer bloodstream retention time than the marketed formulation, Taxotere® (Composition 15), the present invention could increase the drug retention time in the bloodstream over Taxotere® by using the biodegradable and biocompatible polymers of the present invention.

EXAMPLE 53

Pharmacokinetics for the Ca$^{2+}$-Fixed Docetaxel-Containing Polymeric Micelles To compare the bloodstream retention time of the Ca$^{2+}$-fixed docetaxel-containing polymeric micelles with that of the formulations containing other carriers, the compositions were prepared as follows.

(Composition 16) Ca$^{2+}$-Fixed Docetaxel-Containing Polymeric Micelles.

Docetaxel, mPEG-PLA-tocopherol (Mn: 2,000-1,800), and D,L-PLA-COONa (Mn: 1,700) were admixed in a weight ratio of 75.0:25.0:1.0, and then the mixture was dissolved in 5 ml of anhydrous ethanol to prepare a clear solution. Ethanol was removed therefrom using a vacuum evaporator to prepare a docetaxel-containing polymeric composition. Distilled water (4 ml) was added thereto, and the mixture was stirred for 10 minutes at 60° C. to prepare a polymeric micelle aqueous solution containing docetaxel. To the above polymeric micelle solution was added a CaCl$_2$ aqueous solution (concentration: 100 mg/ml) of the same number of equivalents as the D,L-PLA-COONa, and the mixture was stirred for 20 minutes at room temperature. The mixture was passed through a filter with a pore size of 200 nm, and then was lyophilized. The hydrodynamic particle size of the polymeric micelles was 32 nm.

(Composition 15) Composition Containing Docetaxel, Tween 80, and 13% Ethanol

Docetaxel (20 mg) and Tween 80 (520 mg) were dissolved in 1.5 ml of 13% (v/v) ethanol aqueous solution to obtain a clear solution. The solution was passed through a filter having a pore size of 200 nm.

The above composition and the drug contents are summarized in Table 18.

TABLE 18

|  | mPEG-PLA-Tocopherol (mg) | D,L-PLA-COONa (mg) | Docetaxel (mg) | CaCl$_2$ (mg) | Content of docetaxel (mg/ml) |
| --- | --- | --- | --- | --- | --- |
| Comp. 16 | 375.0 | 125.0 | 5.0 | 4.1 | 1.0 |

|  | Tween 80 (mg) | 13% aqueous ethanol (ml) | Docetaxel (mg) |  | Content of docetaxel (mg/ml) |
| --- | --- | --- | --- | --- | --- |
| Comp. 15 | 520 | 1.5 | 20.0 | — | 1.0 |

For the animal experiments, male Sprague-Dawley rats weighing 230-250 g were cannulated in the vena femoralis and aorta femoralis. Compositions 16 and 15 were injected into the vena femoralis at a dose of 5 mg/kg over 15 seconds. After the injection, 0.3 ml of the whole blood was taken from the aorta femoralis in 1, 5, 15, and 30 minutes, and in 1, 2, 3, 4, and 6 hours, and then centrifuged to obtain clear supernatant plasma.

The plasma drug concentration was analyzed according to the same process as in Example 36, and the results of the plasma concentrations of the drugs are shown in the following Table 19 and FIG. 13.

TABLE 19

| | Plasma concentration of docetaxel (μg/ml) | | | | | | | | |
|---|---|---|---|---|---|---|---|---|---|
| | 1 m | 5 m | 15 m | 30 m | 1 h | 2 h | 3 h | 4 h | 6 h |
| Com. 16 | 48.2 | 6.16 | 1.22 | 0.51 | 0.28 | 0.13 | 0.08 | 0.06 | 0.06 |
| Com. 15 | 31.8 | 3.89 | 0.69 | 0.24 | 0.07 | 0.003 | — | — | — |

Figure 13:
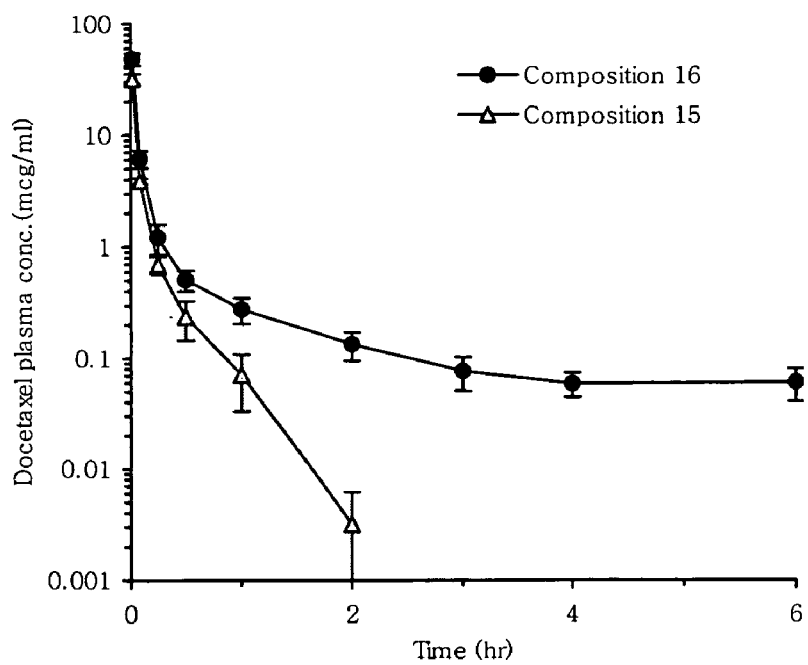
FIG. 13 shows the plasma drug concentration of the docetaxel-containing $Ca^{2+}$-fixed polymeric micelles and Tween 80 preparations (Taxotere®) at various time intervals after administration.
Figure 14A:
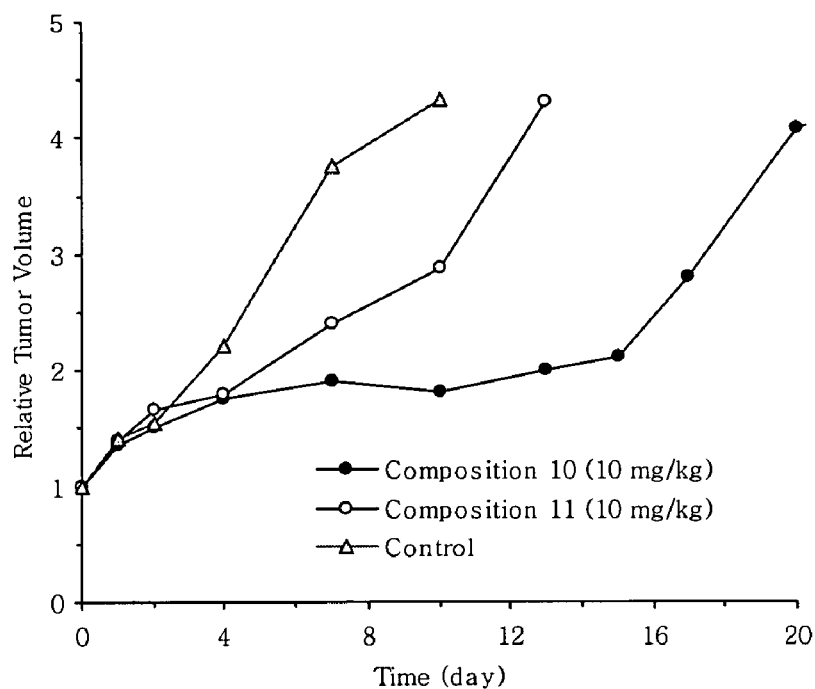
FIG. 14A shows the anticancer effects of the drug containing $Ca^{2+}$-fixed polymeric micelles in mice using the human breast carcinoma cell line MX-1.
Figure 14B:
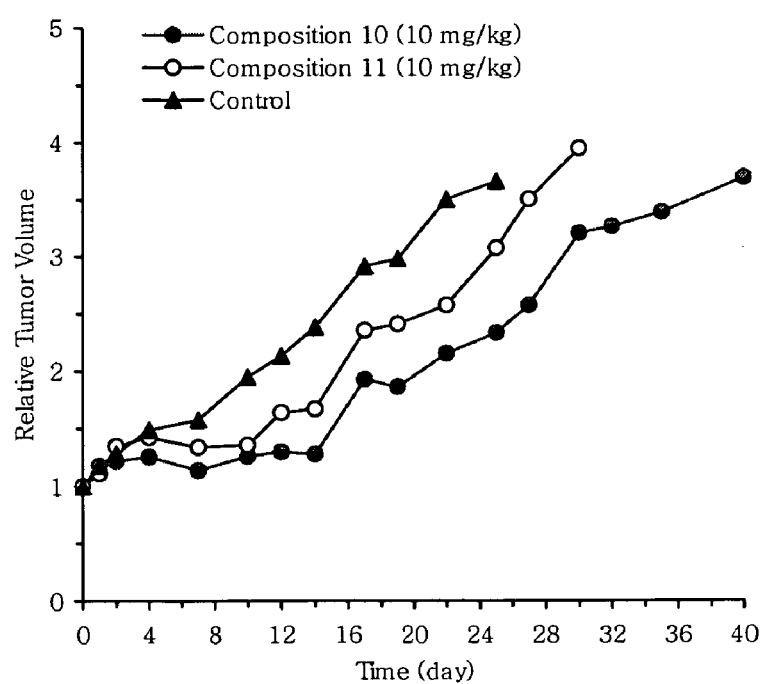
FIG. 14B shows the anticancer effects of the drug containing $Ca^{2+}$-fixed polymeric micelles in mice using the human breast carcinoma cell line MDAMB435S.
Figure 14C:
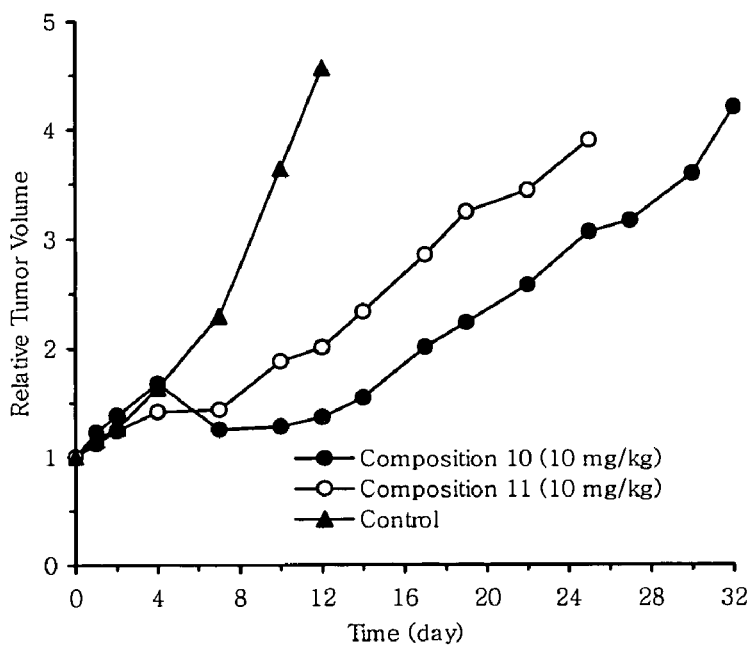
FIG. 14C shows the anticancer effects of the drug containing $Ca^{2+}$-fixed polymeric micelles in mice using the human ovarian carcinoma cell line SKOV-3.
Figure 14D:
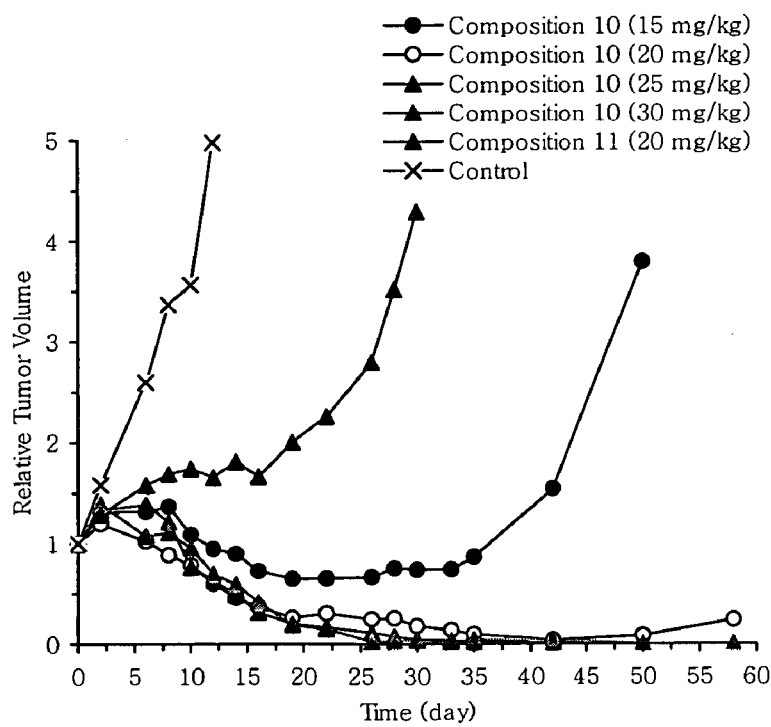
FIG. 14D shows the anticancer effects of the drug containing $Ca^{2+}$-fixed polymeric micelles in mice using the human ovarian carcinoma cell line SKOV-3.
Figure 14E:
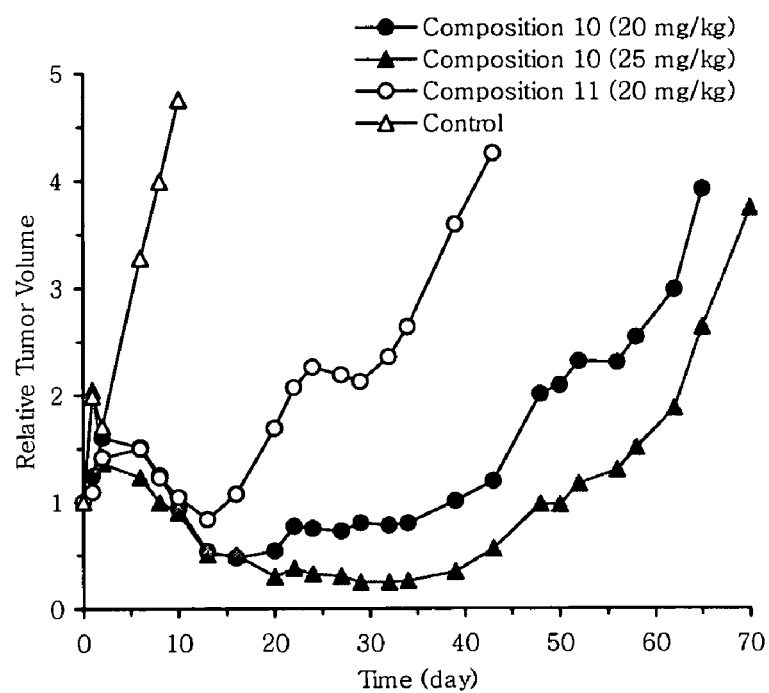
FIG. 14E shows the anticancer effects of the drug containing $Ca^{2+}$-fixed polymeric micelles in mice using the human colon carcinoma cell line HT-29 (3 cycles)
Figure 14F:
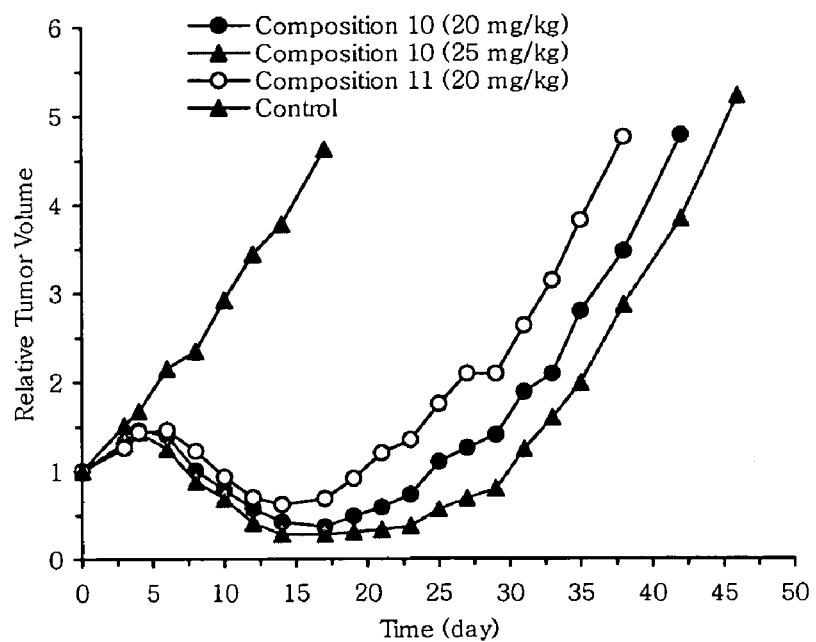
FIG. 14F shows the anticancer effects of the drug containing $Ca^{2+}$-fixed polymeric micelles in mice using the human colon carcinoma cell line HT-29.
Figure 14G:
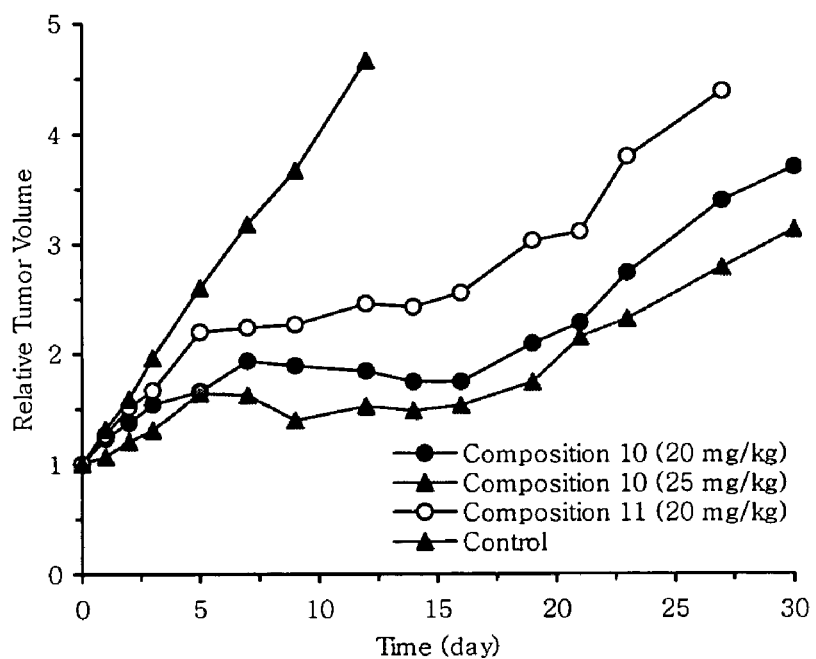
FIG. 14G shows the anticancer effects of the drug containing $Ca^{2+}$-fixed polymeric micelles in mice using the human prostatic carcinoma cell line PC3.
Figure 14H:
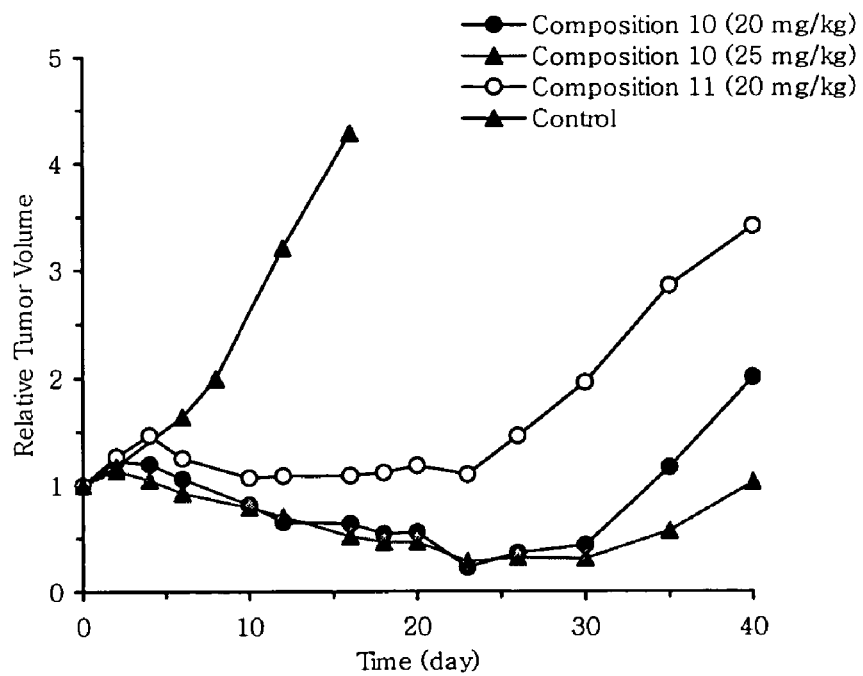
FIG. 14H shows the anticancer effects of the drug containing $Ca^{2+}$-fixed polymeric micelles in mice using the human brain carcinoma cell line U-373MG.

As shown in Table 19 and FIG. 13, the $Ca^{2+}$-fixed polymeric micelles (Composition 16) had a longer bloodstream retention time than the injections containing Tween 80 (Composition 15). Since the $Ca^{2+}$-fixed polymeric micelles (Composition 16) of the present invention had a longer bloodstream retention time than the marketed formulation, Taxotere® (Composition 15), the present invention could increase the drug retention time in the bloodstream over Taxotere® by using the biodegradable and biocompatible polymers of the present invention.

EXAMPLE 54

Maximum Tolerated Dose of the $Ca^{2+}$-Fixed Paclitaxel-Containing Polymeric Micelles Ten (10) groups of Tac:Cr:(Ncr)-nu athymic mice (female, 8 weeks, 20.5±0.50 g; male, 8 weeks, 21.3±1.6) were given by i.v. injection through the tail vein, on a 0-, 1-, and 2-day schedule, of the $Ca^{2+}$-fixed paclitaxel-containing polymeric micelle solution (Composition 10) at doses of 16, 20, 25, and 30 mg/kg. Mice survival and variation in the body weights were observed daily over 30 days in all the groups.

Five (5) groups of Tac:Cr:(Ncr)-nu athymic mice (female, 8 weeks, 24.7±1.2; male, 8 weeks, 24.2±1.3) were given by i.v. injection through the tail vein, on a 0-, 2-, and 4-day schedule, the $Ca^{2+}$-fixed paclitaxel-containing polymeric micelle solution (Composition 10) at doses of 20, 25, 30, and 35 mg/kg. Mice survival and variation in body weight was observed daily over 30 days in all the groups.

Four (4) groups of Tac:Cr:(Ncr)-nu athymic mice (female, 8 weeks, 22.5±0.8;male, 8 weeks, 24.3±1.6) were given by i.v. injection through the tail vein, on a 0-, 2-, 4-, and 6-day schedule, the $Ca^{2+}$-fixed paclitaxel-containing polymeric micelle solution (Composition 10) at doses of 20, 25, and 30 mg/kg. Mice survival and variation in body weight was observed daily over 30 days in all the groups.

Ten (10) groups of Tac:Cr:(Ncr)-nu athymic mice (female, 8 weeks, 19.3±0.71 g; male, 8 weeks, 23.3±1.1) were given by i.v. injections through the tail vein on a 0-, 4-, and 8-day schedule, the $Ca^{2+}$-fixed paclitaxel-containing polymeric micelle solution (Composition 10) at each doses of 25, 28, 30, 35, and 39 mg/kg. Mice survival and variation in body weight was observed daily over 30 days in all groups.

The MTD was defined as the allowance of a median body weight loss of approximately 10-20% of the control, while causing neither death due to toxic effects nor a remarkable change in the vital signs within 2 weeks after the drug administration. As shown in Table 20, the MTD in each dosing schedule was in a range of 20-30 mg/kg.

A vehicle toxicity study was also done. The animals receiving drug-free $Ca^{2+}$-fixed polymeric micelles grew rapidly, and gained slightly more weight than the animals receiving saline or not having injection. This was attributed to the calorie contents of the formulation.

TABLE 20

| Dosing Schedule (day) | Number of animals | MTD (mg/kg/inj.) | | Maximum BW change (%) | |
|---|---|---|---|---|---|
| | | Male | Female | Male | Female |
| 0, 1, 2 (q1d × 3) | 5 | 25 | 25 | −17.7 | −16.3 |
| 0, 2, 4 (q2d × 3) | 5 | 30 | 30 | −17.6 | −15.0 |
| 0, 2, 4, 6 (q2d × 4) | 5 | 20 | 20 | −11.5 | −10.2 |
| 0, 4, 8 (q4d × 3) | 6 | 35 | 35 | −8.5 | −8.0 |

EXAMPLE 55

Anticancer Activity of $Ca^{2+}$-Fixed Paclitaxel-Containing Polymeric Micelles

Cells were taken from storage in liquid nitrogen, and established as an in vitro cell culture. After the harvesting, the cells were washed in sterile phosphate buffered saline (PBS), and the number of viable cells was determined. Cells were re-suspended in sterile PBS at the approximate concentration of $7 \times 10^7$ cells/ml. Healthy nude (nu/nu) athymic mice (20-25 g, 8-week aged) were injected subcutaneously in the right flank with 0.1 ml of a cell suspension containing $7 \times 10^6$ human cancer cells (MX-1, SKOV-3, MDAMB435S, HT29, PC-3, U373MG). After the cancers reached a certain size, they were xenografted three times to form xenograft fragments of 3-4 mm. The xenograft fragments were subcutaneously injected into the right flank of healthy nude (nu/nu) athymic mice (20-25 g, 8-week aged) with a 12 gauge trocar needles. When the volumes of the cancers reached 100-300 mm³, the drug was administered, and this point of time was recorded as day 0. At day 0, the mice were divided into 5 groups, and at days 0, 1, and 2, at days 0, 2, and 4, or at days 0, 4, and 8, the metal ion-fixed polymeric micelles (Composition 10) and the Cremophor EL formulation (Composition 11) were administered with various doses of paclitaxel through the tail vein, and the volumes of the cancers were measured at different time intervals. The volumes of the cancers were calculated by the formula $(W^2 \times L)/2$ wherein W is a short axis, and L is a long axis.

For the evaluation of treatment, tumor volumes were calculated as follows:

Tumor volumes (TV)=$0.5 \times L \times W^2$ (L: long axis, W: short axis)

Relative tumor volume (RTV)=$(V_t/V_0) \times 100\%$ (Vt: TV on day t, V0: TV on day 0)

Treatment efficacy was determined by 3 criteria used in parallel: mean tumor growth curves, optimal growth inhibition (T/C %), and specific growth delay (SGD)

The optimal growth inhibition at a particular day within 4 weeks after the last injection was calculated from the mean of the RTV values of treated versus control groups multiplied by 100% (T/C %)

The SGD was calculated over one and two doubling times as follows:

Specific Growth Delay (SGD): SGD=($T_D$ treated–$T_D$ control)/$T_D$ control $T_D$: Tumor-doubling time The levels of activity are defined as follows:

| | T/C % | | SGD |
|---|---|---|---|
| (+) | <50 | or | >1.0 |
| + | <50 | and | >1.0 |
| ++ | <40 | and | >1.5 |
| +++ | <25 | and | >2.0 |
| ++++ | <10 | and | >3.0 |

According to NCI standards, a T/C≦42% is the minimum level for activity. A T/C<10% is considered as a high anti-tumor activity level justifying further development.

For an experiment to be considered evaluable, there were at least 4 mice per treatment to the control group and at least 4 tumors per group. At the start of the treatment, the minimum tumor diameter was 4 mm or a volume of 30 mm³. The animals dying within 2 weeks after the final drug administration were considered as toxic deaths, and were excluded from any evaluation. The treatment groups with more than 1 in 3 toxic deaths or a median body weight loss of more than 15% without complete recovery was considered not evaluable for antitumor efficacy.

As shown in FIGS. 14a-14h and Table 21, both the metal ion-fixed polymeric micelle-treated group and the Cremophor EL formulation-treated group showed a considerable inhibition rate on cancer growth compared with the control group, and particularly, the metal ion-fixed polymeric micelle (Composition 10)-treated group showed a higher inhibition rate than the Cremophor EL formulation (Composition 11)-treated group.

EXAMPLE 56

Anticancer Activity of $Ca^{2+}$-Fixed Paclitaxel-Containing Polymeric Micelles against Taxol® Resistant Cancer Animal Model Cells were taken from storage in liquid nitrogen, and established as an in vitro cell culture. After the harvesting, the cells were washed in sterile phosphate buffered saline (PBS), and the numbers of viable cells were determined. The cells were re-suspended in sterile PBS at the approximate concentration of 7×10⁷ cells/ml. Healthy nude (nu/nu) athymic mice (20-25 g, 8-week aged) were injected subcutaneously in the right flank with 0.1 ml of a cell suspension containing 7×10⁶ human cancer cells (HT29). After the cancers reached a certain size, they were xenografted three times to form xenograft fragments of 3-4 min. The xenograft fragments were subcutaneously injected into the right flank of healthy nude (nu/nu) athymic mice (20-25 g, 8-week aged) with a 12 gauge trocar needles. When the volumes of the cancers reached a certain size, the paclitaxel (Cremophor EL formulation, Taxol®) was administered at a dose of 20 mg/kg/day under the dosing schedule of qldX5 through the tail vein. After 3 weeks, the drug was administered at the dose of 20 mg/kg/day under the dosing schedule of qldX5 again to obtain a xenograft fragment of Taxol® resistant cancer. After the cancers reached a certain size, the xenograft fragments (3-4 mm) were subcutaneously injected into the right flank of healthy nude (nu/nu) athymic mice (20-25 g, 8-week aged) with 12 gauge trocar needles. When the volumes of the cancers reached 100-300 mm³, the drug was administered, and this point of time was recorded as day 0. At day 0, the mice were divided into 5 groups, and at days 0, 2 and 4, the metal ion-fixed polymeric micelles (Composition 10) and the Cremophor EL formulation (Composition 11) were administered with various doses of paclitaxel through the tail vein, and the volumes of the cancers were measured at different time intervals.

TABLE 21

| Cancer cell line | Dose (mg/kg) | Dosing Schedule (day) | N | T/C % Comp. 10 | T/C % Comp. 11 | SGD Comp. 10 | SGD Comp. 11 | Activity level Comp. 10 | Activity level Comp. 11 |
|---|---|---|---|---|---|---|---|---|---|
| MX-1 | 10 | 0, 1, 2 (q1d × 3) | 5 | 22.9 | 47.0 | 2.25 | 0.75 | ++ | (+) |
| SKOV-3 | 10 | 0, 1, 2 (q1d × 3) | 5 | 25.8 | 36.6 | 1.80 | 1.0 | ++ | (+) |
| | 15 | 0, 2, 4 (q2d × 3) | 7 | 10.9 | NA | 4.5 | NA | ++++ | NA |
| | 20 | 0, 2, 4 (q2d × 3) | 7 | 1.7 | 28.0 | >>8.7 | 1.0 | ++++ | ++ |
| | 25 | 0, 2, 4 (q2d × 3) | 7 | 1.8 | NA | >>8.7 | NA | ++++ | NA |
| | 30 | 0, 2, 4 (q2d × 3) | 7 | 1.4 | NA | >>8.7 | NA | ++++ | NA |
| MDAMB435S | 10 | 0, 1, 2 (q1d × 3) | 5 | 53.5 | 70.0 | 1.0 | 0.45 | — | — |
| HT-29 (3 cycles) | 20 | 0, 4, 8 (q4d × 3 × 3 cycles) | 10 | 7.9 | 14.7 | 4.5 | 3.5 | ++++ | +++ |
| | 25 | 0, 4, 8 (q4d × 3 × 3 cycles) | 10 | 5.9 | NA | 4.8 | NA | ++++ | NA |
| HT-29 (3 cycle) | 20 | 0, 4, 8 (q4d × 3) | 10 | 3.4 | 10.4 | 11.0 | 4.5 | ++++ | +++ |
| | 25 | 0, 4, 8 (q4d × 3) | 10 | 1.0 | NA | 14.8 | NA | ++++ | NA |
| PC-3 | 20 | 0, 4, 8 (q4d × 3) | 10 | 27.7 | 40.1 | 5.3 | 0.7 | +++ | + |
| | 25 | 0, 4, 8 (q4d × 3) | 10 | 23.0 | NA | 6.0 | NA | +++ | NA |
| U373MG | 20 | 0, 4, 8 (q4d × 3) | 10 | 3.5 | 15.8 | 4.0 | 2.8 | ++++ | +++ |
| | 25 | 0, 4, 8 (q4d × 3) | 10 | 2.5 | NA | >>4.0 | NA | ++++ | NA |

(* 3 cycles: A single i.v. dose of the drugs in saline was administered intravenously on days 0, 4, 8 (1 cycle), 21, 25, 29 (2 cycles), 42, 46 and 50 (3 cycles)

As described in the above experiment, to demonstrate the effectiveness of the metal ion-fixed polymeric micelles against the Taxol®-resistant cancer, an animal model for in vivo anti-cancer activity against Taxol®-resistant cancer was established. When cancer cells inoculated into mice were exposed repeatedly to Taxol®, $IC_{50}$ of paclitaxel for Taxol®-pretreated cancer cells was increased significantly compared to that of paclitaxel for the native cancer cells (data not shown). In this animal model, the metal ion-fixed polymeric micelle (Composition 10)-treated group showed a higher inhibition rate than the Cremophor EL formulation (Composition 11)-treated group possibly due to the longer retention in the bloodstream of an effective concentration of the drug incorporated in the metal ion-fixed polymeric micelle as shown in FIG. 15 and Table 22.

reached a certain size (500-700 mg), the cancer graft was cut into 3×3×3 mm pieces, and transplanted with trocar needles, and then, passaged for 3 times to form xenograft fragments of 3-4 mm. The xenograft fragments were subcutaneously injected into the right flank of healthy nude (nu/nu) athymic mice (20-25 g, 8-week aged) with 12 gauge trocar needles. When the volumes of the cancers reached 100-300 mm³, the drug was administered, and this point of time was recorded as day 0. At day 0, the mice were divided into 5 groups, and at days 0, 2 and 4, the metal ion-fixed polymeric micelles (Composition 10) and Cremophor EL preparation (Composition 11) were administered at a dose of 20 mg/kg of paclitaxel through the tail vein. The volumes of cancers were measured at different time intervals.

TABLE 22

| Cancer cell line | Dose (mg/kg) | Dosing Schedule (day) | n | T/C % Comp. 10 | T/C % Comp. 11 | SGD Comp. 10 | SGD Comp. 11 | Activity level Comp. 10 | Activity level Comp. 11 |
|---|---|---|---|---|---|---|---|---|---|
| Taxol® pretreated HT-29 | 20 | 0,2,4 (q2d × 3) | 5 | 17.6 | 29.0 | 3.2 | 2.0 | +++ | ++ |
| | 30 | 0,2,4 (q2d × 3) | 5 | 15.1 | NA | 3.8 | NA | +++ | NA |

EXAMPLE 57

Anticancer Activity of $Ca^{2+}$-Fixed Paclitaxel-Containing Polymeric Micelles Against Doxorubicin Resistant Cancer Animal Model Human uterus sarcoma, doxorubicin (Adriamycin®) resistant subline (MES-SA/Dx5; MDR variant), was purchased from American Type Culture Collection (ATCC), and cultivated and isolated in RPMI-1640 medium supplemented with 10% FBS. After harvesting, the cells were washed in sterile phosphate buffered saline (PBS), and the numbers of viable cells were determined. The cells were re-suspended in sterile PBS at the approximate concentration of 7×10⁷ cells/ml. Healthy nude (nu/nu) athymic mice (20-25 g, 8-week aged) were injected subcutaneously in the right flank with 0.1 ml of cell suspension containing 7×10⁶ human cancer cells (MES-SA/Dx5). After the cancers As described in the above experiment, to demonstrate the effectiveness of metal ion-fixed polymeric micelles against the doxorubicin-resistant cancer, an animal model for in vivo anti-cancer activity against doxorubicin-resistant cancer was established. In this animal model, the metal ion-fixed polymeric micelle (Composition 10)-treated group showed a higher inhibition rate than the Cremophor EL formulation (Composition 11)-treated group possibly due to the longer retention in the bloodstream of an effective concentration of the drug incorporated in the metal ion-fixed polymeric micelle as shown in FIG. 16 and Table 23.

TABLE 23

| Cancer cell line | Dose (mg/kg) | Dosing Schedule (day) | n | T/C % Comp. 10 | T/C % Comp. 11 | SGD Comp. 10 | SGD Comp. 11 | Activity level Comp. 10 | Activity level Comp. 11 |
|---|---|---|---|---|---|---|---|---|---|
| MES-SA/D × 5 | 20 | 0, 2, 4 (q2d × 3) | 5 | 7.3 | 19.4 | 6.0 | 2.5 | ++++ | +++ |

The polymeric micelles prepared from the amphiphilic block copolymer according to the present invention is harmless, and has a high drug entrapping rate and retains a drug in an aqueous solution for an extended period of time, and therefore, can increase the drug plasma concentration when injected into the body.

In addition, the polymeric compositions of the present invention can form stable polymeric micelles or nanoparticles in body fluids or aqueous solutions. The micelles or nanoparticles formed from the compositions of the present invention have a hydrophilic outer shell and a hydrophobic inner core wherein a large amount of hydrophobic drug can be physically trapped. The drug-containing micelles and nanoparticles of the present invention have a prolonged retention time in the bloodstream after administration, and can be utilized to make various pharmaceutical formulations.

It is to be understood that the above-described embodiments are only illustrative of application of the principles of the present invention. Numerous modifications and alternative embodiments can be derived without departing from the spirit and scope of the present invention, and the appended claims are intended to cover such modifications and arrangements. Thus, while the present invention has been shown in the drawings and is fully described above with particularity and detail in connection with what is presently deemed to be the most practical and preferred embodiment(s) of the present invention, it will be apparent to those of ordinary skill in the art that numerous modifications can be made without departing from the principles and concepts of the present invention as set forth in the claims.

What is claimed is:

1. A block copolymer comprising hydrophilic A blocks and hydrophobic B blocks with a terminal hydroxyl group, wherein said terminal hydroxyl group of the hydrophobic block is substituted with tocopherol or cholesterol, wherein the hydrophilic A block is a member selected from the group consisting of polyalkylene glycols, polyvinyl alcohols, polyvinyl pyrrolidones, and polyacryl amides wherein the hydrophobic B block is a member selected from the group consisting of polylactides, polyglycolides, polycaprolactone, polydioxan-2-one, polylactic-co-glycolide, polylactic-co-dioxan-2-one, polylactic-co-caprolactone and polyglycolic-co-caprolacton.

2. The block copolymer according to claim 1, which is an A-B type diblock copolymer or a B-A-B type triblock copolymer.

3. The block copolymer according to claim 1, wherein the ratio of the hydrophilic A block to the hydrophobic B block is within the range of 30:70 to 97:3 by weight.

4. The block copolymer according to claim 1, wherein the hydrophilic A block has a number average molecular weight of 200 to 50,000 Daltons.

5. The block copolymer according to claim 1, wherein the hydrophobic B block has a weight average molecular weight of 50 to 50,000 Daltons.

6. A block copolymer, which is represented by the following formula:

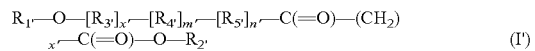  (I')

wherein $R_{1'}$ is $CH_3$—, $H$—$[R_{5'}]_{n'}$—$[R_{4'}]_{m'}$—, or $R_{2'}$—O—$C(=O)$—$(CH_2)_{x'}$—$C(=O)$—$[R_{5'}]_{n'}$—$[R_{4'}]_{m'}$—;

$R_{2'}$ is tocopherol or cholesterol;

$R_{3'}$ is —$CH_2CH_2$—O—, —$CH(OH)$—$CH_2$—, —$CH(C(=O)$—$NH_2)$—$CH_2$—, or

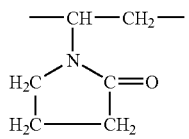

$R_{4'}$ is —$C(=O)$—$CHZ'$-O—, wherein $Z'$ is a hydrogen atom or methyl group;

$R_{5'}$ is —$C(=O)$—$CHY''$—O—, wherein $Y''$ is a hydrogen atom or methyl group, —$C(=O)$—$CH_2CH_2CH_2CH_2CH_2$—O—, or —$C(=O)$—$CH_2OCH_2CH_2$—O—;

l' is an integer from 4-1150;

m' is an integer from 1-300;

n' is an integer from 0-300; and

X' is an integer from 0-4.

7. A drug carrier comprised essentially of block copolymer according to claim 1.

* * * * *